US012793847B2

(12) United States Patent
Staples, II et al.

(10) Patent No.: US 12,793,847 B2
(45) Date of Patent: Nov. 10, 2026

(54) INTELLIGENT ECOSYSTEM

(71) Applicant: CERNER INNOVATION, INC., Kansas City, KS (US)

(72) Inventors: Alan H. Staples, II, Shawnee, KS (US); David E. Voyles, Kansas City, KS (US)

(73) Assignee: CERNER INNOVATION, INC., Kansas City, MO (US)

( * ) Notice: Subject to any disclaimer, the term of this patent is extended or adjusted under 35 U.S.C. 154(b) by 1229 days.

(21) Appl. No.: 17/135,116

(22) Filed: Dec. 28, 2020

(65) Prior Publication Data

US 2021/0202093 A1 Jul. 1, 2021

Related U.S. Application Data

(60) Provisional application No. 62/955,803, filed on Dec. 31, 2019.

(51) Int. Cl.
*G16H 50/20* (2018.01)
*G06F 17/18* (2006.01)
(Continued)

(52) U.S. Cl.
CPC ............. *G16H 50/20* (2018.01); *G06F 17/18* (2013.01); *G16H 10/60* (2018.01); *G16H 50/70* (2018.01)

(58) Field of Classification Search
CPC ........ G16H 50/20; G16H 10/60; G16H 50/70; G06F 17/18
See application file for complete search history.

(56) References Cited

U.S. PATENT DOCUMENTS 7,117,185 B1 * 10/2006 Aliferis .................. G06N 20/00 706/14
12,665,088 B2 * 6/2026 Pagi ....................... G16H 50/20
(Continued)

FOREIGN PATENT DOCUMENTS

WO WO-2018223005 A1 * 12/2018 ............. A61K 31/37

OTHER PUBLICATIONS

Johnson et al (Machine_Learning_and_Decision_Support_in_Critical_Care) (Year: 2016).*

*Primary Examiner* — Mamon Obeid
(74) *Attorney, Agent, or Firm* — Invoke

(57) ABSTRACT

Systems, methods, and devices identify members of a cohort, as one example. In embodiments, medical professionals may seek to identify patents who suffer from, or are likely to suffer from, a condition, even if patients are not associated with a diagnoses or a recorded description of the condition, or medical professionals may seek to confirm the inclusion of members in a cohort. Embodiments include considering hypothetical factors that may indicate whether a patient has a condition, performing regression analyses to obtain a set of initial cohorts and likelihoods that they will experience the condition, and user interaction(s) to identify members, for example patients with a higher likelihood of developing a condition. Outputs include, in embodiments, treatment plans or updates for a patent such as medications or appointments, tests to be performed on physical samples, or input(s) for a manufacturing process, such as three-dimensional printing using biological or other materials.

24 Claims, 6 Drawing Sheets

(51) Int. Cl.
*G16H 10/60* (2018.01)
*G16H 50/70* (2018.01)

(56) References Cited

U.S. PATENT DOCUMENTS

| | | | | |
|---|---|---|---|---|
| 2009/0055217 | A1* | 2/2009 | Grichnik | G16H 50/30 705/2 |
| 2009/0216558 | A1* | 8/2009 | Reisman | G16H 40/67 705/3 |
| 2011/0301479 | A1* | 12/2011 | Ghanem | A61B 5/7275 600/515 |
| 2012/0059779 | A1* | 3/2012 | Syed | G06N 20/00 706/12 |
| 2014/0046683 | A1* | 2/2014 | Michelson | G06F 19/3437 705/2 |
| 2015/0112722 | A1* | 4/2015 | Dees | A61B 5/7275 705/3 |
| 2015/0313529 | A1* | 11/2015 | Nevo | A61B 5/4809 600/595 |
| 2016/0188843 | A1 | 6/2016 | Staples et al. | |
| 2016/0328525 | A1* | 11/2016 | Gross | A61B 5/14542 |
| 2017/0308981 | A1* | 10/2017 | Razavian | G16H 40/60 |
| 2018/0322955 | A1* | 11/2018 | Sevenster | G16H 50/20 |
| 2018/0368737 | A1* | 12/2018 | Bonomi | A61B 5/7264 |
| 2019/0385744 | A1* | 12/2019 | Freeman | G16H 80/00 |
| 2020/0024669 | A1* | 1/2020 | Spetzler | G16H 20/10 |
| 2021/0391079 | A1* | 12/2021 | Clifton | G06N 3/09 |
| 2022/0285027 | A1* | 9/2022 | Gossens | G06N 20/10 |
| 2024/0412871 | A1* | 12/2024 | Mathur | G16H 50/30 |
| 2024/0417803 | A1* | 12/2024 | Menschikowski | C12Q 1/6886 |
| 2025/0132039 | A1* | 4/2025 | Wellmann | G16H 20/10 |
| 2025/0316391 | A1* | 10/2025 | Mathur | G06N 20/00 |
| 2026/0053433 | A1* | 2/2026 | Ramanathan | A61B 5/4818 |

* cited by examiner

400

INTELLIGENT ECOSYSTEM

CROSS-REFERENCE TO RELATED APPLICATIONS

This Application claims the benefit of U.S. Provisional Application No. 62/955,803, filed Dec. 31, 2019, incorporated herein by reference.

BACKGROUND

Systems and devices used to implement actions, such as systems used during a medical diagnosis or testing, use known inputs, such as a group of patents with a known condition represented by a standard label, for example, or a group of known tests to be performed on a sample. Such systems may return a previous diagnosis or known conditions designated with recognized labels. Systems may only identify a small or under-representative set of patients or perform limited tests, or fail direct actions to complete constructing items, or otherwise be limited by relying on known inputs. In a medical research or treatment context, for example, a cohort of patients can be identified with a certain condition, for purposes of further study or publication, for example, based on prior diagnoses, even though many conditions or tests to be performed, for example, may not be labeled or provided in one or more medical records accessible to a medical professional.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief and at a high level, this disclosure describes, among other things, methods, systems, and computer-storage media for implementing patient treatment or other actions, for example. Embodiments of the present invention include unconventional systems, devices, and methods, which solve existing problems in the art relating to limited analyses of people and items where certain data records or points (or categorization or conclusions based on data, such as a diagnoses), or potential substitute materials, are not known. Embodiments include systems that use factors relating to a population group or a set of accepted inputs that are characterized by one or more factors to identify additional members of the population group or additional acceptable material inputs. For example, systems described herein prescribe a medication or schedule appointments with medical professionals based as part of information output by the system. In some cases systems direct the performance of additional tests such as tissue, fluid, and/or genetic tests, where tests can be performed by one or more devices within a system (or able to receive results or commands from a system). In some embodiments, a system includes combinations of devices or data sources repositories, including remote and accessible sources, with iteration(s) of analyses that also consider decisions by medical professionals, for example, as part of generating updated lists of cohorts or higher likelihoods of membership in a cohort for one or more individuals or materials.

Systems and devices that operate according to embodiments of the present invention can take advantage of unique structures or availability of data sources, one or more machine-learning techniques such as regression analysis, and/or indications of user interactions, for example the most local, recent, or trending correlations of factors with hypothesized conditions, the most accepted or trending surrogate factors (such as factors suggested by a user or a system as potentially relevant to, correlating to, or indicating that a condition is likely to be present now or in the future) or the most local or recent surrogate factors (for example by region or by medical treatment facility), and/or the most weighted considerations based on human intervention or other information, for example using a hierarchy or tagged data with respect to components such as a user intervention component, discussed below. The improved systems disclosed herein include improvements to the operation of systems and devices that may conduct or publish research or implement other actions, for example planning or triaging in emergencies or unusual situations, or in new locations, where more recent or more local information in a system may be more relevant and can be weighted.

In embodiments, a system is used to determine the likelihood that one or more patients have a condition or are likely to have a condition, because the patients may have been misdiagnosed or a professional may not have recorded a diagnosis (or not recorded it in a record available to the system or in a standard format used by the system). In some cases, a system according to embodiments of the invention provides a set of individuals or other candidates that are likely to have a condition, for example ranked by the likelihood that each has the condition, and this first set can be refined one or more times as new information is accessed by the system, including records of user interactions, or because of an expected event such as the individual being scheduled to undergo a procedure or be released from treatment, for example. In embodiments, a trend or change in the likelihood of an individual developing or having a condition is determined, for example based on factors associated with the condition, which may be flagged or cause an action such an updated treatment plan or a visit by a medical professional.

In embodiments of the present invention, one purpose is to provide one or more predictions relating to patient(s) or other individuals in a population group regarding condition(s), for example the likelihood that each patient in a set (e.g., at a hospital, or in an out-patient program, or in social group identified by a researcher) has a condition or will develop a condition, for example in the next 30 or 90 days, or in the next 3 years, depending on the statistical significance of the relationships in the data according to embodiments or as set by a user. The predictions can be based on analyzing factors associated with one or more patients known to have the condition, then looking for one or more of those factors in the subject patient. Certain factors will correlate more (or correlate more recently or more locally, or be weighted by a user or the system) and thus indicate more of a likelihood that the patient has or will have the condition. Systems disclosed herein can be the primary driver or resource for providing potential factors for users to consider, for example so that medical researchers or professionals can benefit from the data accessible to the system and be provided with factors that have relationships or potential relationships with a condition. Embodiments allow an individual researcher or medical professional to benefit from improved use of, and access to, data regarding patients with conditions (or materials or physical tests with characteristics). Because the system can determine suggestions to present to users at various steps, including when defining the factors to be analyzed by a cohort engine or the patients to be included for an analyses, users do not need their own access to underling patient or other medical data, and users do not need to identify subtle or imperceptible relationships in the data in order to test a hypothesis. Embodiments of the system access data regarding individual items such as patients that may be restricted, as well as known information in a field, to determine and display new information to a user, in some cases providing new suggestions or relationships with respect to previously-analyzed data, because the system is able to automatically look at previously-unidentified factors or patients in various data sets, less-noticeable or less-visible relationships, or information in view of one or more manual actions over time (to exclude data, or confirm or change a diagnosis, etc.).

In some cases, an initial prediction is updated based on machine-learning techniques such as a regression analyses and/or new data such as events or user selections, or on an adjustment of the factors used or weighted, and a trend or uptick in the risk of a condition is identified, which can change a medication, treatment, or appointment schedule, for example. The factors are displayed in some cases, for example if a user selects to view the factors considered, and the user can remove one or more factors for one or more (or all) patients, or remove one or more patients, thereby providing new information for a regression analysis or other analysis (such as a set of multiple machine-learning processes) to use to update the likelihoods returned by the system during future use of the system. As one example, where a factor relating to Opioid Use Disorder (OUD) such as a respiratory revival is actually due to an unrelated drug interaction, a user may remove that patient (or that factor for that patient), which a system uses to learn or refine its analyses and in some cases update or push changes to treatment plans or medications, for example.

In other embodiments in accordance with the present invention, systems identify a set of individuals or other candidates to be included in a group, in some cases along with each candidates likelihood of inclusion based on certain factors, which can be viewed or adjusted by a user, or updated by a system. A system may use adjusted factors, or indications from users that certain factor(s) or candidate(s) should be removed or included (for the duration of one or more requests or going forward), to learn and refine its analysis and to generate a second or updated set of candidates (such as an updated set of cohorts), in some cases with higher likelihoods of having a condition and belonging in a group. Systems can act as a cohort engine to provide, suggest, and update initial sets of cohorts associated with a condition.

In some embodiments of the present invention, a system including one or more computing devices receives a selection of a candidate, for example an individual person, and a selection of a condition. A system according to embodiments can visually display, including graphically, an increase or decrease in the risk or likelihood of the candidate having the condition, for example to identify an increase within a certain time frame, in some cases prior to a condition (for example where the condition is a heart problem requiring hospitalization, and a factor such as losing employment or a change in diet has caused a trend or spike in the likelihood of the candidate incurring the condition). In some cases, a user can be pushed a warning or update that flags such an increase, and the user can view or select to view more information, such as which factors or rules in the system changed in that time frame (for example to see that a loss of employment is indicated, or that a diet change was recorded, and that one or more of these factors contributed to an increase, and by how much). A user can discount or remove certain factors for one or more patients, which can be used to train a system, and which can also be recorded (for example as part of a user interaction component) so that future users can view user interactions with respect to a factor or patient as one reasons for a change in the prediction for that patient over time.

BRIEF DESCRIPTION OF THE DRAWINGS

Embodiments are described in detail below with reference to the attached drawing figures, wherein.

DETAILED DESCRIPTION

Figure 1:
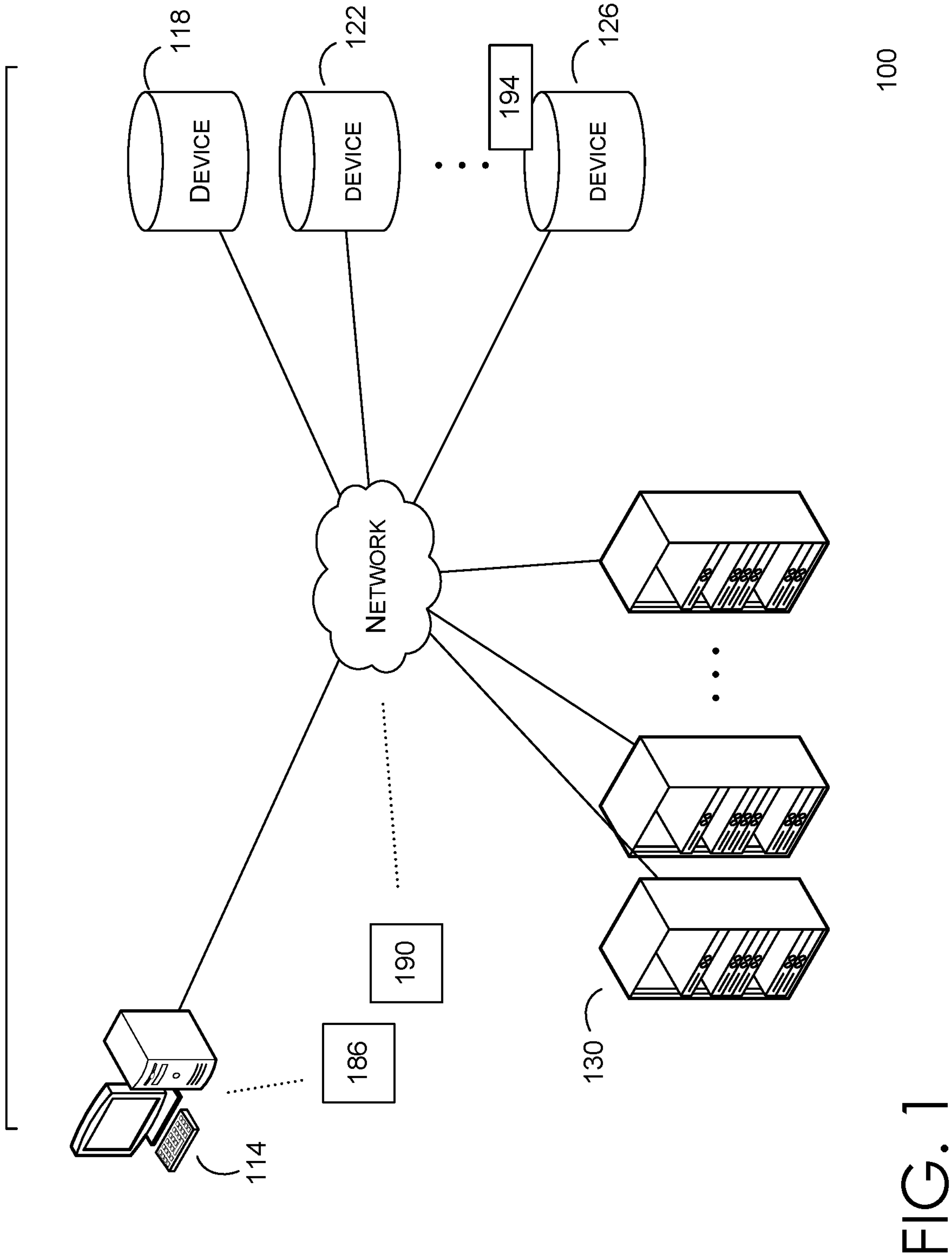
FIG. 1 is a block diagram of an exemplary computing environment suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

There are needs for improved systems and devices such as embodiments of the present invention that identify likely members of a cohort, including analyses to determine likely members of a cohort with a certain degree of accuracy or certainty, and including a time-based aspect so that a user can compare the likelihood (for example of membership in a cohort, according to one or more confidence levels displayed by system 200, discussed below) at different points in time or changes over time, for individual members such as a patient, or for groups of members, for example by demographic information such as age or gender. Embodiments allow users such as medical professionals, researchers, or other professionals to determine a group of candidates or members that should or could be part of a set even though one or more members lack a standard identification as a member of the set, based on other known information about the members. Improvements to systems and devices described herein provide suggested or predicted known information to consider as part of determining members of a cohort based on the identification or description of the cohort, data sources and analyses, correlations seen among known or likely members, and/or correlations between suggested known or unknown factors, which could be discovered by a system over time based on data including records or receipt of manual actions by professionals.

In some cases, embodiments relate to unknown conditions, such as a diagnosis or treatment in a medical context, for example, with new implementations of resources relating to other factors about a patient, for example, in combination, in some cases with machine-learning analyses such as regression analyses or information based on human interaction(s) used in iteration. Embodiments utilize other factors to predict or suggest a condition that is not known, or to display such predictions with indications of likelihood, for example as made available by components or devices, nor do they suggest additional factors that are not known or indicated by a user, for example, based on correlations of factors with a condition or other factors (such as those identified). Systems implemented with conventional arrangements of known considerations, in the context of data available to a system, are not structured or indicated so that certain parameters or sets of inputs are updated and acted on in a manner that prioritizes or maximizes analyses of unknown conditions for professionals, such as health care professionals. As one example, it has been suggested that a small percentage (e.g., in single digits, in some cases) of individuals with certain conditions have received a diagnosis, meaning a recorded or understandable diagnosis that is recognized by system 110 in embodiments.

Embodiment of improved systems described here accommodate users such as curators and end users, for example, where aspects of the system, even where involving distributed devices, can be presented to various users under certain limitations or anonymizations, for example for compliance or privacy, while still furthering diagnoses, research or other goals. In some cases, embodiments expose the most-recent, local, trending, or otherwise most-useful factors that can be used to determine candidates for membership in a group (such as patients with a recorded diagnosis), nor do they provide values for unknown conditions, such as the likelihood of incurring a condition, for example to efficiently push or provide actions by a system. In some examples, a low rate of diagnosis in a population or group may be expected for conditions where a label may be a sensitive issue (such as OUD or Alzheimer's), but low rates of diagnosis have been reported for other conditions, as well, such as types of arthritis or other conditions, for example, due to low rates of adoption of standard labels or codes, and/or because third-parties such as insurance companies do not base reimbursement or otherwise rely on labels or codes to identify conditions, for example.

Embodiments of the invention integrate disparate resources or functions relating to a known condition and potentially related factors for determining an unknown condition, such as a missing diagnosis or an unavailable material input, or a test that could have been ordered based on the amount of a physical sample that is being used or destroyed by testing. Some embodiments include methods and/or devices that incorporate techniques (e.g., regression analyses) or implement updates, or indicate values for the likelihood of a condition according to multiple, simultaneous factors, for example in systems that provide treatments such medications, appointments, or diagnosis-related updates to electronic medical records (EMRs). Embodiments can provide inputs based on analyses of distributed resources, for example for real-time production such as three-dimensional printing or tissue or sample analyzing and treatment that can be based on, or accommodate, an unknown consideration. Embodiments can certify actions such as diagnoses or edits, in addition to implementing treatment-option plans or interfaces, or provide interfaces where users may select to view deeper or supplemental results in records or a publication, for example. Systems in embodiments are able to effectively use computing or data resources during analyses of patients or testing of samples, for example, including in some cases computing device(s) with options to implement actions such as diagnoses, predictions, tests, or input-materials, for example, such as when scheduling appointments or using a limited or fragile physical sample, or during a sensitive process where unknown conditions must be predicted in order to continue.

FIG. 1 illustrates an exemplary environment 100 including system 110. System 110 includes one or more devices, e.g. computing device 114, hypothesizing device 118, and server device 130. Devices such as computing device 114 and other devices used in accordance with embodiments of the present invention can include computing devices such as mobile computing devices, laptop or desktop computing devices, server or database devices, and/or other computing hardware devices as understood by those skilled in the art, in some cases with devices or components distributed among more than one physical device or including access of remote computing or data-storage sources. Embodiments and devices or components included therein may be further described or delineated in one or more claims, specific to certain embodiment(s), regarding organizational, structural, or functional aspects of systems as claimed, in some cases.

Figure 2:
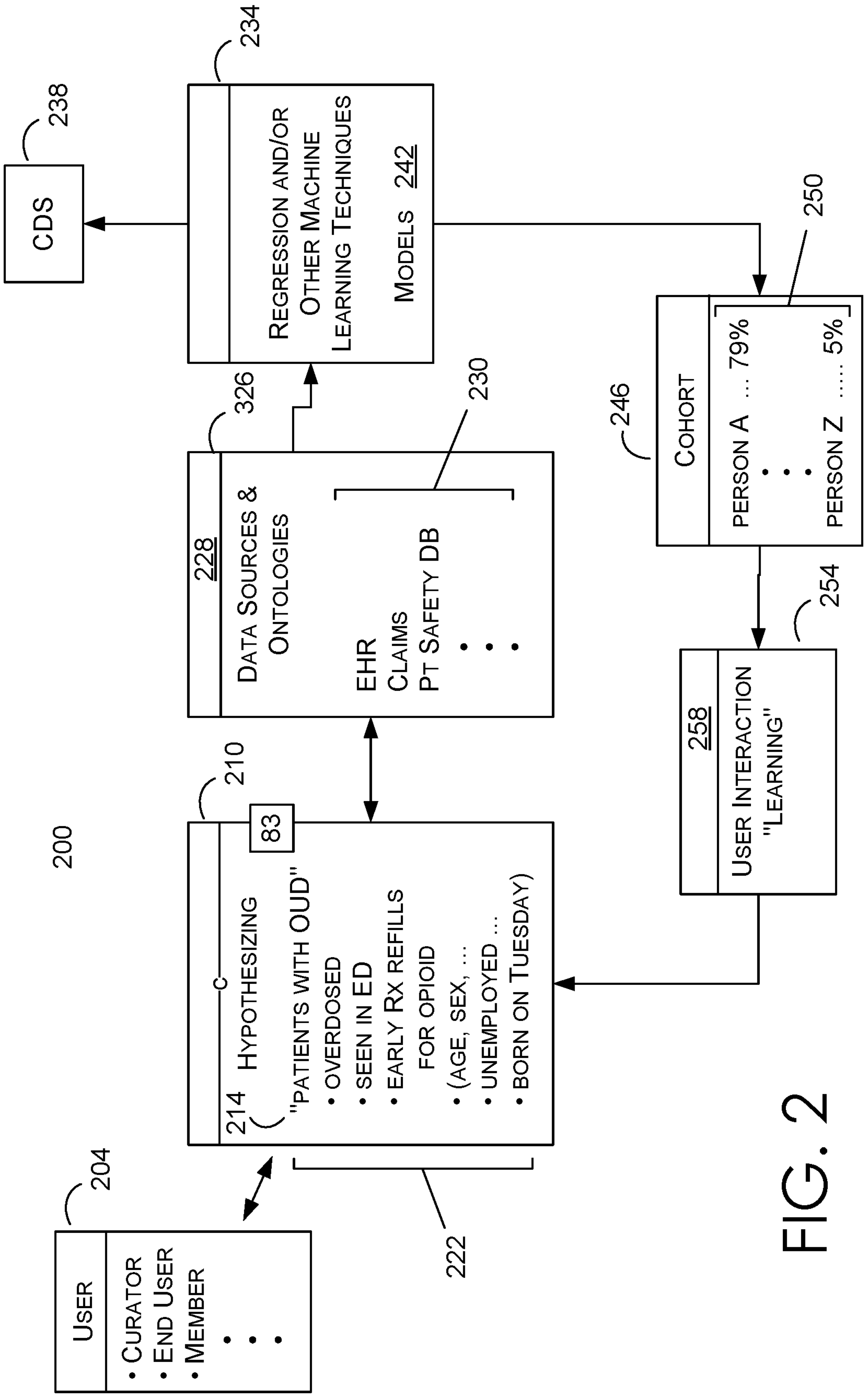
FIG. 2 is an exemplary diagram of components suitable to implement embodiments of the present invention.

A user (for example user 204 as shown in FIG. 2) may have access to a device such as computing device 114, which is a mobile device in some embodiments, for example a secure mobile device used by medical professionals in a clinical setting, or a portable device with specialized or secured access to programs or applications operating with the benefit of a system such as system 110. Computing device 114 accesses certain resources or components, such as hypothesizing component 210 in FIG. 2, data sources component 236 in FIG. 2, and regression component 234 in FIG. 2, respectively, which may be servers, databases, or devices with certain layers or cross-sections of data from various sources, discussed in more detail below. System 100 includes outputs, such as output 186, also described in more detail below, which can indicate or cause action 190. Each resource or component (e.g., data source component 226, etc.), can be associated with a tag, such as tag 194, also discussed in more detail below. Server device 130 in this example is one or more servers or computing devices that can be accessed by or in communication with other devices in system 110, for example hypothesizing component 210 in FIG. 2, to provide, for example, patient record data such data as from EMRs, factors and factor data, and/or research or other accessible information, for example as pulled from sets of patient records, programmed preconditions or data obtained according to set rules, or as indicated by recent or cited research, in some cases.

As an example, system 110 provides a cohort engine that prevents events such as current medical conditions or future medical conditions for a set of patients. If a cohort engine as described herein according to embodiments is used to identify all patents with OUD or with a high likelihood (over a certain threshold) of having or developing OUD in the future, then a medical professional can use this information to manage pain treatment, or system 110 can perform an action of creating or updating a medical treatment plan, for example. An initial cohort as discussed below can include patients that have a disorder along with those determined to have a certain likelihood or higher of having or developing the disorder. System 110 uses factors from across devices in the system or otherwise accessible by system 110 to inform an initial set of cohorts that system 110 and/or to refine a set of cohorts over time. In some cases, an initial set of cohorts are tests or analyses to be performed on a sample, or known inputs to be used in an automated manufacturing or printing process, and system 110 update or supplement the tests or inputs in order to maximize testing of a sample or to substitute input materials, for example, as discussed below.

Factors can include data, such as demographic data for an individual such as a patient or a member of a cohort such as list of cohorts 250 (e.g., age, gender, height, etc.), habits or characteristics (e.g., smoker, occupation, etc.), patient data such as examination results or observations (e.g., temperature, current blood pressure, patient-reported information by date, etc.), refusals of treatments or follow-ups, requests by patients by date, social data such as employment, home or work environment characteristics, or other factors describing circumstances, predispositions, or exposures relating to an individual, as examples. For instance, factors can include data regarding an individual's surroundings, such as temperature or other data from a "smart" appliance or fixture, such as a thermostat from a location where an individual spends time and/or controls the settings, and/or data regarding habits, such as workout or recovery data from an application on a mobile device associated with the individual, or purchase history data associated with the individual's identity or credit card. Factors can also include any data points that may make a condition, or a symptom or characteristic of a condition, more or less likely. In embodiments, a condition is a diagnosis or disease or disorder, and a condition can include likely behaviors, habits, or other characteristics that may be useful to identify, for example individuals likely to begin or quit smoking, or individuals likely to exercise or take vitamins.

As stated, computing device 114 in FIG. 1 can provide output 186, and, in embodiments, computing device 114 (or another device connected to computing device 114) uses output 186 from system 110 to perform one or more actions. Actions include, for example, providing a set of patients with a likelihood of having a condition, including or identifying patients that did not receive a diagnosis, or a recording of a diagnosis, for the condition. Embodiments can provide a value for an unknown consideration, such as unknown value for a diagnosis of OUD, by flagging or listing a set of patients that includes one or more patients likely to suffer from OUD at the present time or at some other time, such as in the future, as discussed below with respect to FIG. 2.

Output 186 can include actions such as implementing a new or adjusted medication routine or other treatment, or providing results or records to a third party such as a publisher or regulatory body, as discussed. In another example, a new or updated form such as an EMR form for a user 204 to interact with on a device, such as computing device 114, can be outputted by system 200, in some cases pre-populated with a value such as a code or name for a predicted diagnosis with a probability above a certain threshold value, such as 75%, or an output 186 can include an additional or activated with a predicted or likely value. In some cases, a new structure or code to be used by a resource such as hypothesizing component 210 is output by system 200, for example to add a field for certain EMRs based on qualifying criteria (e.g., demographics, medication use, current physical symptom, etc.) and/or to flag or push an update to one or more devices in system 200 regarding the addition. One or more users 204 can take actions to provide feedback to system 110, and/or professionals in the field such as clinical settings or home health care professionals can provide feedback, which can be used by system 110 as part of a user interaction component, for example user interaction component 254 in FIG. 2.

User interaction via user interaction component 254, such as feedback, may be received from non-clinical professionals, for example one or more non-clinical subject matter experts who may take steps, for example, to curate, facilitate, and/or train the system. As another example, a source of feedback used by system 110 may be non-experts, such as laypeople or other participants, such as an individual predicted to be part of a cohort providing feedback. For instance, an individual can be predicted by system 110 to be part of a cohort, in some cases with a certain percentage or likelihood of certainty, which system 110 (via the user interaction component) can use to automatically access contact information, generate, and send a message, such as an SMS text message or an email, to the individual. In response, the individual can indicate that they are not part of a cohort, or provide other information that the system 110 can consider in order to exclude or further evaluate the individual as a potential member of a cohort or not. In this example, an individual's response is received by user interaction component 254. For example, an individual could authorize the release of specific medical information using the user interaction component 254.

Output 186 can include providing a user interface 600 such as a display of one or more patients along with suggested or provisional diagnoses; displaying a set of patients likely to suffer from a condition even though they have not been diagnosed with the condition; providing a diagnosis field for a provisional or predicted diagnosis in a form to a medical professional that indicates a likelihood of accuracy; and/or entering a treatment plan item, prescription order, or appointment for a patient. A cohort or group with a condition includes those that meet certain criteria even if the condition or group as defined does not (and will not) share the precise label of such a condition. For example, a medical professional can request to see patients with (or likely to have) back pain in order to consider patients for a new study. System 200, when determining patients known to be in the group or as potential cohorts, can look for terms relating to backs or back pain within data, such as claims filed and other medical and billing forms, and system 200 can include patients in a group of patients known (or likely) to have back pain based on more general terms and characteristics than a precise label or diagnosis of "back pain," such as patients with back surgeries in the past five years or receiving certain types of physical therapy. In some embodiments, computing device 114 or a connected device obtains or uses a physical input (such as a substitute for known physical input(s) by a three-dimensional printer), or performs one or more actions, such as chemical, medical, or genetic tests, on a sample, based on unknown considerations. In some cases, the actions are in addition to a set of requested or known actions (such as tests to be run on a tissue or blood sample). In some cases, the actions are automatically selected based on a finite remaining sample and/or time frame for performing actions (which is one example of relying on unknown considerations, including to some extent prior human interactions, to perform actions where the opportunity to perform the actions could be missed by prior systems).

The exemplary devices in FIG. 1 are shown in an illustrative computing environment. Hypothesizing device 118 in FIG. 1 is associated with a hypothesizing component 210, as discussed below with respect to FIG. 2, in an embodiment. Similarly, components illustrated in FIG. 2 such as regression component 234 are associated with one or more devices as shown in FIG. 1, in this example regression device 126. One or more devices, such as computing device 114 and hypothesizing device 118, or other devices shown or not shown, such as a mobile or other computing device including a display with a user interface 600, are associated with an initial cohort 250 with percentages such as 79% and 5%, and a user-interaction aspect 254, as shown in the example in FIG. 2. Although computing devices including computing device 114, and resource device 118, etc., such as devices providing computing functionality including databases and servers, can be known devices as understood by one of skill in the art, their implementations and uses are not known. Embodiments described herein improve the functioning of one or more aspects of a system, including systems with distributed aspects and in some cases with mobile or remote components. Devices such as data source device 122, regression device 126, etc., can be housed one or using the same computing device, distributed, or access distributed information. Embodiments of system 110 include recording user interactions and using that data as part of a system that takes actions on, for example, medical records, treatment plans, and physical samples.

A known condition in accordance with embodiments is a condition that is set or recognized, such as a disease that has been diagnosed or recorded (or recorded properly) as diagnosed, such as by using a Systematized Nomenclature of Medicine—Clinical Terms ("SNOMED CT" or "SNOMED") code or a Prescription Drug Monitoring Program (PDMP) code or label or another description that is set or recognized by a system, for example eye or dental health systems or codes, chemistry or pharmacological references, academic or other standards, or other sources.

In some cases, a known condition is a set of one or more analyses to be performed on a physical sample such as tissue, DNA, or soil, in a situation where a system can provide one or more additional analyses to be considered or performed on the sample based on the remaining portion or conditions of the sample, including in real time, or based on the portion of the sample that would have been destroyed or damaged by the analyses set to be performed, and/or based on factors associated with one or more of the analyses set to be performed and other data sources, as used by embodiments of a system described herein. As one example, a medical testing device can include or be in communication with computing device 114, and it may be communicated to system 110 that a medical testing device has or will have leftover or extra sample material that could be tested further (and may be wasted or damaged if not, for example in real time). Therefore system 110 can provide one or more tests to be performed, such as tests on biological or food samples, in some cases, for carcinogens or toxins, nutritional values, genetic information or expression, etc. In other examples, a construction device such a printer may need to timely identify substitute material(s) to use as input(s), where system 110 can consider the properties of an intended input versus properties of substitute inputs, and system 110 can also consider the purpose or application of the inputs to weight certain properties or combinations of properties associated with one or more substitute inputs.

In other cases, a known condition is a set of one or more known or accepted input materials used in a production process, such as three-dimensional printing, where sufficient substitute materials (including organic materials) are selected to maximize certain parameters such as effectiveness, cost, permeability, etc., based on factors that represent characteristics of known, acceptable input materials. In one example, such a system can quickly identify substitute or candidate materials for use in production processes that may be time sensitive (such as printing tissue with cellular and biological inputs, or producing including etching of semiconductor surfaces, etc.). Such a system may overcome a language or other barrier by recognizing that another available input material is considered equivalent or acceptable, to a certain degree of likelihood, and a user can view the factors and data sources that contributed to the list or ranking of the candidate, substitute materials.

Unknown conditions can be unknown diagnoses (where a patient does not have a diagnosis for a condition, or where a user has opted to audit or confirm or study the diagnosis and considers it unknown). As one example, if a user, for example a medical provider or another risk- or resource-planner, seeks to understand which patients or population members have a condition such as opioid use disorder (OUD), the data returned may be grossly under-inclusive, for one or more reasons. In some cases, a medical provider provides treatment that indicates a condition without applying an official code or label, such as SNOMED code or label for OUD or another condition, that a system can rely on to provide all patients with the condition.

Or, for example, unknown conditions can be tests to be performed on available material samples or substitute materials that are available and/or meet certain performance or cost measures. Unknown conditions can exist for various reasons. For example, a condition or diagnosis may be missing due to unavailable patient records or data. For the example of the condition of OUD, a stigma may exist with this diagnosis that causes medical professionals to avoid making this diagnosis official or under the proper SNOMED designation or code, so that a population group has a much higher instance of the disorder than apparent using known designations for the disorder. In some cases, the billing or claims information for a medical condition may provide a diagnosis or make one evident, but this information may not be recorded in a medical record for future reference by medical treatment software or professionals. Or a patient may have been treated in a location or during a time period where SNOMED codes or other labels were not used for a particular condition, or the medical professionals at the time or location did not use a code as a practice or due to other constraints, or a language barrier or other difference renders a diagnosis of a certain condition unavailable to a system or unreliable, for example because a diagnosis is defined with one or more terms in another language or dialect or defined too narrowly or too broadly, or by one or more incorrect factors, at a previous time or location that is associated with a patient's medical records.

In some cases a medical professional may avoid giving or entering diagnosis of a certain condition, or "passively" diagnoses a condition by not recording it officially or using codes, and/or making the condition apparent based on treatment or other notes without using a specific designation, for example to avoid disputes, penalties, stigmas, or other repercussions for a patient or healthcare facility or provider. There are times when a user such as a research professional has access to partial data for privacy or other reasons, where a known diagnosis is not accessible, or not matched with patients. In some cases, a known condition is not clearly defined, so even a known condition by one definition, or as understood by one or more treating medical professionals or other entities, has not become a known condition in an accessible or recognized medical record or field of a medical record. Therefore a substantial portion of patients even known or likely to have a disorder by one or more medical professionals could be missing the data or proper records to be identified as having the disorder using known designations such as SNOMED labels. Factors such as respiratory depression and revival in response to an overdose, which may correlate strongly with OUD, could be performed with different treatments or medications, or recorded using various software programs provided by one or more entities, and embodiments of the present invention can identify these various underlying treatments or circumstances under one factor (or one condition) so that a user 204 does not need to be aware of each possible recording or version of a factor or condition within record, for example, or does not miss identifying patients that are potentially positive for a certain factor or condition.

An unknown test or procedure to be used on a physical sample may be unknown because a user did not know how much sample would be available or useable at the point of testing, or because a user preferred to let a system determine the remaining tests based on the tests selected and other data accessed and analyzed by the system. An unknown input material may be unknown because a planned input became depleted, expensive, unusable, or unavailable for some reason, for example due to certain concerns or changes by a user or as recommended or pushed to users by a system, which a user can input into the system or accept (for example as user interaction or as part of defining or modifying a condition), in order to shift or filter substitute input materials identified by the system to meet an adjusted standard. Similar adjustments can be made in the context of medical conditions (for example where a user is seeking patients with a known condition as adjusted or in combination with some other characteristic), or in the context of sample testing, where a user or system can indicate a secondary goal or consideration relating to any additional testing to be recommended or implemented by the system.

Unknown conditions can be a missing or unknown diagnosis this represents a pathology test result or other type of test result, where hypothesizing component 210 and/or other aspects of system 200 are used, in some cases in addition to examination data or other information about treatment or care (for example from an appointment), to generate possible test result including probabilities for the test results and/or a treatment plan based on the possible test results, as output 186. Output 186 is a notification or trigger for approval in embodiments, for example approval by user 204 that adds authorization to an action (such as one or more additional tests) by system 200 or provides a record regarding approval or confirmation.

As one example, a patient who has not been labeled with a diagnosis in a medical record or in an accessible medical record, but who has been revived for an opioid overdose in the past, may not be included as a patient likely to suffer from OUD, but in embodiments system 110 can determine the patient is likely to suffer from OUD with certainty above, for example, 75%, or likely to suffer from OUD with a certainty above an even higher percentage within a certain time frame of the revival event, for example within three months of the event. In embodiments, this one factor or consideration relating to revival from an overdose is confirmed by human interaction, as described below, to be a factor that should currently and/or in the future be used to indicate OUD in certain circumstances (or not in other circumstances), which system 110 can learn over time. For example, a medical professional or researcher can analyze individuals in the general population or based on the medical records or information available, or based on a micro-population such as patients in a medical facility or study. A user can remove a certain patient from an initial cohort of patients likely to suffer from OUD if that patient's specific revival event was based on another cause besides overdoes, such as a drug interaction. In other cases, an entire factor, for example a certain pattern of filling prescriptions or making appointments by a patient, could also be used or suggested by system 110 to be used along with revival event information, to more effectively analyze population groups with unknown diagnoses for OUD, in this example.

In some cases, an entire factor may be deemed irrelevant or not accurately correlated by system 110, in some cases in whole or in part based on machine learning, for example if a researcher takes actions that system 110 determine to be human interactions that indicate a factor is not properly correlated or not desired to be correlated with a certain condition (e.g., if a false-positive correlation is found for patients who purchase generic versus name-brand medications, system 110 could learn or determine that this factor is not an actual indicator of OUD, even if it displays a facial correlation at some point). Aspects of embodiments of the present invention use data blending to present and/or refine an initial cohort of patients or, for example, analyses to be performed on a physical sample. Various factors used by system 110 to determine predicted conditions or other values can be weighted by timeliness, proximity, specific circumstances such as demographic data (age, gender, etc.), or other relationships determined by system 110 or proposed by researchers or medical professionals. In embodiments, system 200 identifies n-number of factors for analysis while applying m-number of machine-learning practices, in order to identify one or more combinations of factors that produce the most utility in cohorting.

Output 186, for example, is a diagnosis or a likelihood of a diagnosis recorded for a patient, or a treatment plan (including updates to treatment plans), which can include indications of the likelihood of certainty for each underlying basis for aspects of a diagnosis or plan. An update may be ordered or received pre- or post-surgery based on known considerations such as diagnoses, along with values for unknown considerations such as predicted diagnoses for any missing diagnoses, and provided in association with output 186 by system 200. An update is ordered in some cases due to increased risks or changed circumstances, or after a patient has relocated due to the possibility of less-familiar conditions to a patient, for example. An update may be ordered or received based on a lapse of time since a prior update or check for updates, or since a change of a certain magnitude in system 200, in some cases a change relating to certain conditions or factors or certain population groups.

As an example, output 186 is an appointment that is calendared or requested with respect to a patient, such as with a specialist or a certain type of therapist, or a visit by a social worker or other professional. In some cases, output 186 is a setting to re-run, confirm, or further address results associated with output 186, for example because certain factors about a patient were recorded immediately following an event such a disease, or before a first treatment had been implemented for a threshold period of time. In other embodiments, output 186 includes material for publication such as an updated table of data or graphical representation of data representing a group of individuals, factors, conditions, etc., including over time in some cases, and such material can be automatically pushed or triggered for approval to be pushed onto an online platform or publication, where versions of representations of data over time, or as filtered or viewed by factors, patients and/or the likelihood of conditions, can be made available via selection by a user 205 via an interface 600.

In some cases, an output 186 can include multiple sets of data, for example a first set associated with a higher percentage of known information, for example research or treatment data that may be used for compliance or publication, and a second set associated with a lower percentage of known information (and including more conditions set according to probabilities based on factors besides or in contradiction with a diagnosis, for example) that may be used for other actions, such as resource planning by a treatment facility, community messaging and alerts, quarantine procedures, preventative measure, etc. Actions by a system according to embodiments are presented with options and/or indicators of risks such as side effects, combination warnings, or other possibilities that have or also have a relatively high or similar likelihood of being present.

Systems and devices according to embodiments that identify likely members of a cohort 250, for example, include a time-based aspect that can be associated with the factors 222 considered over time, so that the predicted conditions and/or associated probabilities for a specific patient at various time points can be compared to each other, for example to identify trends, such as sharp trends (for example trends increasing above a certain rate) in risk. In some cases, a list of cohorts 250 in ranked order by probability, or an output 186, enables a professional or a facility to prioritize patients or resources for treatment, release, relocation, emergency-preparedness, or other activities or preferences.

Embodiments allow users such as medical professionals, researchers, or other professionals to determine a group of candidates or members that should be considered part of a set even though one or more members lack a standard identification as a member of the set, based on known information about the members. Improvements to systems and devices as described herein provide suggested or predicted information to consider as part of determining members of a cohort, based on the identification of the cohort, data sources and analyses, correlations among known or likely members of a cohort, and/or correlations between known and potentially-suggested factors, which could be discovered by a system over time based on records or the receipt of manual actions by professionals, for example, as considered or weighted during an iterative process, in some cases.

In some cases, a user such as a curator of the information in system 110, for example, can remove a factor for an individual patient or for an entire hypothetical condition for a set of patients, as discussed. Removed factors can be stored for later use and system 110 can continue to analyze one or more removed factors for new correlations or potential correlations in order to present the factors (in some cases again) to a user if conditions change, for example if system 110 detects a new, statistically-significant indication of a relationship between a factor and a condition, or if the defining criteria for a factor change in the profession. In embodiments, when a patient is removed from initial cohort 250 according to user interaction, that patient's likelihood for a secondary or other conditions may increase or be flagged.

FIG. 2 illustrates a diagram of components of an exemplary system 200 according to embodiments of the present invention. FIG. 2 includes a hypothesizing component 210, which can display or include a condition 214 selected by user 204, for example patients with OUD, which can be displayed as having 83 members, in this example. Condition 214 can include various factors 222 as shown associated with hypothesizing component 210. A medical researcher or other professional can establish factors 222 as part of a study to find additional factors or patients, or an entity that evaluates risk may rely on system 200 to provide or know factors 222 for a condition 214.

Data source component 226 includes one or more data sources 230, such as EMRs for a patient at issue and/or other patients, claims database(s) relating to medical treatment or other incidents, and/or third-party databases including, for example, patient safety databases, background or demographic reports, criminal or civil action records, and other public or private records associated with one or more patients (for example, employment information, food purchases, self-reported travel including through social media accounts, which can be verified accounts in some cases), locations (for example, chemical or weather exposures in areas overlapping with one or more patients, pollen counts, etc.), and/or timing or conditions (such as outbreaks, seasonal issues, influx or reduction of certain population groups, changes in medications or treatments available or used in an area or time frame, etc.).

In some cases, data sources include information recorded or stored using various types of commercial or public computing programs that may introduce variations. System 200 can identify such variations and address them by identifying or including individuals with diagnoses recorded or observed using different types of programs as a set of initial cohorts (in some cases as refined by one or more interaction using system 200, and in some cases as informed by user interaction module 254). In some cases, data source component 226 analyzes records that include such differences or overlap and identifies factors or individuals despite the variations. Ontologies or other resources can be used by data source component 226, for example as one of several data sources 230, in order to align record from disparate sources or formats so that a user 204 can rely on as many records for as many factors as possible and clearly visualize patients or other candidates in a group, in some cases according to their likelihood of membership in the group.

Data source component 226 is in communication with hypothesizing component 210 and regression component 234, in the exemplary embodiment illustrated in FIG. 2. Various regression models 242 can be used alone or in combination by regression component 234, for example in order to deploy one or more machine-learning algorithms to utilize regarding feedback and/or new data, such as logistic regression models, linear regression models, random models, and/or decision-tree based models. In embodiments, regressions are implemented using historical or stored data within system 200, or accessible by system 200 such as remote medical records, and in some cases a model of models (e.g., one or more other models) is used by system 200. Regression models 242 are examples of a type of models implemented by system 200 but this is merely an example. System 200 can identify one or more factors or features to analyze and apply one or more machine-learning techniques to determine which combination of factors or features likely provides utility or the optimal utility in cohorting. For example, system 200 uses n-number of factors and applies m-number of known machine-learning techniques to identify one or more combinations of factors that are useful or likely to be useful in a cohorting analysis.

Exemplary machine-learning techniques can include techniques, for example, algorithms such as an Apriori algorithm, K-Means, back propagation neural network, various regression algorithms (logistic, stepwise, linear, etc.), instance-based algorithms, reinforcement learning, deep learning algorithms, etc. The regression component described herein, such as regression component 234, can, in some cases, comprise models or component(s) for performing one or more machine-learning processes, which can include one or more types of regression analyses.

System 200 can be iterative, and the percentages of likelihood shown for each of the initial cohorts 250 can be adjusted or updated after considerations from user interaction component 254, which can be real-time or current user interactions and/or prior, stored user interactions, influences factors 222 used by hypothesizing component 210 or other aspects of system 200. Additionally, in some cases, one or more regressions by regression component 234 can act on or further refine any adjusted or updated initial cohorts, and this process can be continued. An iterative process may continue to improve predictions such as initial cohort 250 over time due to more considerations based on user interaction component 254, or due to new data regarding one or more factors or patients, or due to improvements to one or more models over time based on feedback such as confirmation rates.

In some cases, system 200 allows a user 204 such as a curator of information or rules associated with system 200 to visualize relationships among data, such as correlations between members or potential members of an initial cohort 250 and various factors 222 including surrogate factors 222, or among the factors including surrogate factors 222 themselves. Visualization can be performed by system 200 using interface 600, and aspects of data blending technologies can be used to allow or provide visualization of data of members of an initial cohort 250 or factors 222 used for an initial cohort 250, and/or any overlap or correlations among data sets, or trends in correlations. Embodiments including data blending or visualization can include technologies disclosed in application Ser. No. 14/584,689, entitled System Assisted Data Blending, filed Dec. 29, 2014, Publ. No. 20160188843, assigned to Applicant and incorporated herein by reference.

At clinical decision support or CDS 238, data such as factors or potential factors are correlated for data significance, in embodiments, which can be part of regression component 234 or another device or component or remotely performed. System can come back and suggest new correlations to use or suggest to a user 204, referred to as surrogate factors 222. System 200 analyzes surrogate factors that are identified by user 204 or as determined by system 200 as having or likely to have a correlation with a condition, in some cases. System 200 can use several data sources 230 in order to analyze the most records as possible for each surrogate factor 222, in order to include or recommend a surrogate factor 222 to user 204. User interaction component 254 in FIG. 2 and the other components in embodiments of the present invention are associated with one or more computing devices shown in FIG. 1 or described herein and may overlap with one or more other components with respect to the computing device(s) used. CDS 238 is a device or component in embodiments that can be housed in or accessed by one or more aspects of system 200 to perform analyses relating to data and/or to maintain data modeling or data-modeling results. CDS 238 can be a clinical decision support component, or another aspect of system 200 implemented relating to data use or analyses in accordance with embodiments. For example, a medical facility such as a hospital can implement clinical decision support, such as CDS 238, to identify, classify, or treat patients as appearing or likely to have opioid use disorder according to embodiments of the present invention, whether or not opioid use disorder has been documented in the patients' health records such as electronic health records.

In one example, condition 214 seeks patients with a likelihood of suffering from OUD based on factors 222, such as early prescription refills and other factors. Hypothesizing component 210 is in communication with data source component 226, which can contain or access information from data sources 230, such as any medical or patient records, public or private sources such as medical journals and scientific publications, unpublished data, insurance or other medical-related form or statement information, or other sources.

In another example, condition 214 seeks input materials similar to a known material, such as an enzyme used for construction of biological materials, for example using three-dimensional printing performed by one or more computing devices. An initial cohort 250 in this example is provided by system 200 and includes potential substitute materials for the enzyme based on its properties and the application at issue. System 200 can return one or more suggested input materials as initial cohort 250 to user 204 via an interface 600, or to computing device 114. The initial cohort 250 in this case can be determined using data sources 230 and refined using a regression component 234, including through an iterative process that includes information based on a user interaction component 254. Computing device 114 in one example communicates with one or more other devices including a three-dimensional printer or other construction device and cause a substitution of materials, including during a construction process. In other cases, researches can use embodiments of system 200 to identify surrogate factors 222 relating to a known input material, in order.

User interaction component 254 in FIG. 2 is an example of a component that may comprise or access one or more devices, included in a distributed architecture in some cases, regarding selections or decisions made by one or more users. A user 204 can be a user with a certain role, such as an end-user type user 204, using system 200 to obtain predicted diagnoses or to identify high-risk patients with respect to a certain condition, in some cases for a certain time frame. A user 204 can also be a curator, such as an entity that provides a system 200 or content or information to be used by system 200, such as patient medical records, claim forms, or other data, and/or that provides rules or machine-learning approaches or updates for system 200. Members as described herein refer to individual people or materials that belong to a group or potentially belong to a group, such as potential members.

User interaction component 254 can provide data that is arranged in a hierarchy or structured to present, flag, or push certain data due to the most-recent human activities or activities that meet user or entity set criteria regarding the weight or inclusion of activities by user interaction component 254. In some cases, user interaction layer 258 of user interaction component 254 provides a layer or cross-section of data that has been pre-selected or requested to be weighted, flagged, or considered by system 200. As one example, user interactions associated with user interaction layer 158 are stored or presented as weighted or considered based on low percentages returned for an initial cohort 250, circumstances such as emergency or undiagnosed situations, or high variability in results including high variability in prior user interactions, which can be determined and displayed for a user. In situations, such as an outbreak of a new condition, or where prior medical records have been damaged or destroyed, user interaction component 254 may be relied upon more by system 200 or a history of user interactions may be flagged and/or viewable by a user. In some cases, an end user's own user interactions can be weighted or flagged over other contributions by users based on user interaction component 254 or in combination with preferences set in system 110, for example, and user interactions by an end user's colleagues also or instead by weighted or flagged, in some cases.

Using a layer 228, for example a hierarchical layer, for one or more components of system 200 (as stored or accessed by one or more devices in the example in FIG. 1 that are associated with such components), can provide more effective access and use of data including pushing of notifications by system 200 while minimizing exposure of the data and security or privacy concerns, leading to superior treatment plans that are updated more effectively, for example. A layer of information associated with one or more components, such as hypothesizing component 210, can be information that has been tagged as based on known considerations only (such as recorded diagnoses), or at least based-in-part above a threshold amount on known considerations, for example for purposes of publication or compliance reporting.

Certain factors accessible by a system such as system 200, or certain patients or conditions, can be indicated with a tag in or more embodiments. Tagged data may be represented as a layer of a component, such as user interaction layer 258 of user interaction component 254 in FIG. 2, or data source layer 228 of data source component 226. Tagged data can be information that system 200 has determined should be flagged for a user to potentially view or act on, or tagged data in human interaction layer 258, for example, can be data that is responsive to a selection or parameter set by a user or other condition, such as data that system 200 has determined may supplement the factors identified by a user at a hypothesizing step.

Systems in accordance with embodiments generate outputs such as factors to be considered, or likelihoods of a condition or diagnosis, based on relationships identified by system 200 among certain factors that are associated with a known condition and other conditions that may potentially be associated or related to the first condition, for example, or among factors associated with a patient with no diagnosis and factors relating to patients known to have a certain diagnosis or condition. In some cases, the initial factors to be correlated or examined for relationships are identified by users, such as providers of systems, and additional factors can be automatically identified and/or analyzed by systems, while in other cases a system 200 identifies initial factors or other conditions based on a user's needs or parameters. In some cases, users identify a condition and a set of patients, and system 200 automatically identifies other condition(s) to determine factors to be used to determine the likelihood of each patient having the condition and presents the results for the patients to user 204. In other cases, system 200 presents one or more factors for inclusion to user 204. In embodiments, the process of identifying other condition(s) is omitted, and system 200 can identify potential factors (or results for a set of patients regarding likelihood of having a condition) using data associated with patients known to have the condition, and by comparing this data to one or more factors associated with each patient in the set of patients.

In one example, embodiments identify an individual as having a certain likelihood of having the condition OUD. In this example, a quadratic or linear regression is performed on a variety of factors or considerations known to the system to be associated with condition(s) or diagnoses related or possibly related to OUD. Embodiments obtain factors or considerations that correlate to a related condition using resources such as local or accessible medical or industry information, research results and/or data, prior analyses, stored records, etc. For example, nomenclatures such as ICD-9 and ICD-10 can provide one or more conditions that are related or likely related to OUD, in some cases based on a hierarchy inherent to nomenclatures or other systems that organize candidate conditions, factors, or cohorts. Nomenclatures include organizations of conditions (or physical substances or physical tests, for example) such as reference materials organized by subject, or tables or lists that have an organizing structure that may provide nearby or similar conditions for consideration. In some cases a "Table of Contents" or a reference table of tensile strength or freezing temperature can be used to identify potential inputs such as materials and to analyze relationships among their characteristics (which can be weighted or excluded by a user, or recognized by a system as relatively more or less critical to a project, or cost-prohibitive, for example). A set of likely related conditions can be similar or equivalent conditions that are characterized differently by different groups of people or locations, for example if a medical facility or a country labeled patients likely afflicted with OUD as having alcohol dependency, or if researchers in certain locations used a broader or different label for OUD, which may be grouped with other condition(s). A known set of materials that are considered potential substitutes can be used by embodiments of system 200 to identify factors that can be used to determine potential or automatically-approved substitutes, for example system 200 can consider commercial examples of materials used by entities to fulfill similar purposes (e.g., multiple materials known to be used to coat semiconductors, or known to be used in countries with certain regulations).

In embodiments, system 200 determines one or more conditions or identifications that correlate or appear associated with a first condition such as OUD (or a material to be used or a test to be conducted, in other examples). System 200 performs analyses, such as calculations or modeling, for example using a quadratic or linear regression model, to compare or data-mine the condition(s) that correlate or appear associated, including one or more factors associated with each of the condition(s). For example, system 200 or user 204 may determine that three conditions are associated with OUD for purposes of an analysis, based on their proximity to OUD in a hierarchal arrangement of conditions, for example according to third-party sources, or based on proximity accounting for nodes and/or levels, in some cases weighting one or more conditions or facts according to the hierarchal arrangement of a known condition and one or more conditions that are related or likely related the known condition. In other cases a set of conditions could be recognized as a group by system 200 or a user 204, for example based on data or literature, or historic diagnoses could be recognized as grouping (or failing to group) one or more conditions that could be related to one or more of the other conditions in a group. Other methods of identifying potentially-related or applicable conditions exist, such as analyzing data for similar symptoms or characteristics, or using machine-learning models or other hypotheses to predict conditions that may lead to common factors showing relationships. Once a set of one or more other conditions have been identified or selected, embodiments analyze these condition(s) and underlying characteristics to discover relationships among the characteristics that can be useful when applied to patients with no diagnosis for a condition (or with a diagnosis to be audited, for example).

Embodiments analyze the condition(s) and/or their associated factors, for example symptoms and other characteristics of patients with a diagnosis of one or more conditions that appear related to OUD (based on a relationship in a recognized organization of conditions, for example). Analyses performed by system 200 can provide a list of factors or features to be looked for in the patient with no diagnosis, or in some cases system provides an indication for the patient of the likelihood of having a condition such as OUD (which can include a likelihood of having or being diagnosed with OUD in the future, such as in the next three months). System 200 can automate determining which factors or characteristics should go into a quadratic or linear regression model and then interact with a user to either reject, accept, or even propose factors (at any stage of an analysis, for example while identifying potential factors to be used or after or during results for one or more patients, which can be reiterated using models and/or feedback). System 200 can automatically attempt one or more modeling techniques to determine which is the most useful or predictive, as demonstrated by results (such as correct diagnoses or statistically-high predictions or correlations) or by feedback (such as user overrides, confirmations, or later diagnoses by medical professionals), for example.

System 200 uses a quadratic or linear regression model in embodiments to provide potential factors or cohorts, and/or to identify potential conditions for patients, in one example, but other models or equations can be implemented to identify relationships or potential significance among conditions and/or their underling factors (e.g., while analyzing EMR data, research data, or other accessible information about conditions and patients). For example, other regression model(s) can be used alone or in combination to analyze data regarding patients that were diagnosed or confirmed as having one or more conditions that appear related to OUD. System 200 can include other considerations as part of its analysis (such as weighting, or feedback, or filtering or results for significance or probabilities or potential complications, for example). In some cases, certain results from applying a quadratic or linear regression model (or another model or calculation) are used in combination with calculations or adjustments, as inputs to potentially improve, limit, or iterate results. Models such as those described can be used to analyze information and determine potential factors or diagnoses, or to determine whether such potential factors or diagnoses have a certainty above an amount, in some cases based on prior diagnoses or iterations against one or more data sets.

Factors identified using system 200 including model(s) such as a quadratic or linear regression model can be applied to information known about one or more individuals such as patients. User 204 can view a likelihood that patients have OUD (including that they will have it within a time frame or will be diagnosed with it within a time frame), based on an analysis of factors relating to one or more conditions (such as a known condition and/or one or more related or possibly-related conditions) and information associated with the patients. As stated, embodiments of system 200 provide a cohort engine to generate potential factors for consideration (whether such factors are associated with the conditions or likely-related conditions considered or not), and/or to generate information relating to patients for consideration by medical professionals including administrators of resource-planning or crisis-response activities).

In one example, a list of one or more factors are presented to a user for inclusion and the user can select certain factor(s) to be considered, or the user can select to view underlying data for factor(s) identified by systems. For example, an embodiment receives a list of factors to be considered based on user input or known research such as recognized symptoms for a condition such as OUD (e.g., vital signs or other physical indicators of addiction or withdrawal relating to opioid abuse), or behaviors that potentially indicate a higher risk of a condition (e.g., seeking multiple prescriptions or refills of opioid medications, in some cases from more than one medical professional or based on certain statements, such as inconsistent explanations). Systems may present a list of one or more potential cohorts or other considerations to be potentially analyzed with respect to patients with a known diagnosis or condition and patients with an unknown diagnosis. For example, an embodiment may determine that a potential relationship or a statistically-significant association exists between another factor for patients diagnosed with a condition such as OUD and patients previously-undiagnosed with OUD and later diagnosed, or likely to be diagnosed based on other results, for example patient data showing missed medical appointments, or missed appointments above a threshold amount, and/or with no notice or rescheduling efforts.

Embodiments can use one or more analyses that are used for other factors, such as those identified by users, to determine and present potential, additional cohorts for a group. In some cases, the candidate cohort(s) are the top tier or percent of results determined by system 200 or those cohorts with a likelihood above a certain threshold. In some cases, each cohort suggested by system 200 (such as a factor to be used for analyses or a patient to be considered for or diagnosed as having a condition) displays a likelihood of certainty or can be selected to see one, or can be selected to view underlying data or information about the factor or patient. For example, the Table described herein can be opened or expanded to view information regarding factors or patients, such as the frequency or significance of any relationship according to the model(s) implemented. In some cases, user 204 sees that a suggested cohort such as a factor or a patient for a diagnosis group is inaccurate, perhaps because the factor showed up for only one patient (but at a high level) that skewed the results, or perhaps because the patients is known to have an alternate condition that explains one or more factors such as symptoms. In one example, patients may be analyzed for inclusion in a group of patients with a diagnosis of a degenerative eye condition. If one patient is known to have an alternative eye condition that explains most factors and/or relationships among factors used to show a potential diagnosis, that patient can be removed from consideration and that patient's medical information can be excluded form analyses relating to the initial, degenerative eye condition. In other cases, system 200 can suggest a factor such as a car accident at night as a potential factor that a user did not recognize as possibly indicting the degenerative eye condition, particularly, for example, if the accident occurs at a young age. User 204 can view information relating to this factor, and user 204 may discover that this factor appears to be included in an analysis based on only two patients, or based on one or more patients where at least one appears to have been driving under the influence. Therefore user 204 can exclude this factor from this analyses or future analyses, for example future analyses involving this eye condition or all eye conditions.

In some cases, a user such as user 204 is given permission to use or access partial information from one or more devices or components, such as data source component 226 or any other component, which can be included or represented in this example by layer 228 of data source component 226. This can improve the performance of systems such as system 200 by allowing certain layers or aspects of data to be considered by user 204, or securely providing or pushing aspects of data user 204, without violating rules or procedures relating to privacy or consent, for example. Layer 228 can include one or more flags or settings indicating or communicating new accessible, weighted, and/or selected data. In some cases, for purposes of system 200 providing updates or being triggered to perform one or more iterations and/or outputs or updates based on the iteration(s). Layer 228 can represent anonymized information or may include information for which consent has been obtained for types of sharing, by purpose or by recipient such as user 204, or by the potentially-identifying characteristics included.

An unknown diagnosis can be determined or selected, for example by designating a diagnosis via a network to update an EMR or by performing another test or setting another appointment, in examples. When certain information may be more recent or useful, according to parameters such as a geographic radius in combination with a time frame (e.g., a 500 mile radius and in the last six months) or a particular symptom, then resources such as data source component 226 can provide information in a manner that allows for faster recognition or accessibility (e.g., as represented by data source layer 228 of data source component 226). In embodiments, a user can set data source layer 228 or a layer of another component or device using controls included in a user interface 600, based on proximity or recentness, for example. As discussed herein, human interactions can be used by systems to learn, improve upon, or confirm initial, potential results for the values of one or more unknown considerations, such as a diagnosis. In some cases, past or selected human interactions received by a human interaction component 254 are considered by a data source component 226, and a data source layer 228 is used to set the characteristics of one or more human interactions to be considered or flagged, such as interactions in certain cities or hospitals, or within certain time periods. Tags can also be associated with updates stemming from one or more components that may impact a pending or recent output.

There are some cases where known conditions such as conditions with a recognized or confirmed diagnosis, can change over time or not be accurate anymore (or were inaccurate at the time of a misdiagnosis, for example). Embodiments can be used to check or audit the accuracy of supposedly known considerations such a diagnosis for a patient group. For example, the system can treat one or more patients with a recorded diagnosis as patients that are indicated as unknown for that diagnosis and implement an embodiment of the invention, in order to obtain an output 186 of cohorts 250 that indicates which patients should remain diagnosed with the condition and the probability of that determination. Conditions relating to mental health or chronic conditions, allergies or other reactions or intolerances, or pain or mobility, for example, can change over time without removals of diagnoses. Factors such as factors 222 can also shift over time, such as factors relating to age, endocrine levels, body fat levels, etc., and the knowledge or body of records available to analyze, or the models used to provide analyses, for example, can also change over time. Embodiments relating to verifying a diagnosis that is considered known or entered can be used to audit a patient group, a facility, or one or more medical professionals, for example if a misdiagnosis or an outdated diagnosis is suspected or flagged by system 200.

In some cases, one or more patients are analyzed by a cohort engine such as system 200 based on data associated with two different points in time, such as data that was available to system 200 at two different points in time. System 200 can determine if a patient would have been diagnosed with a condition at an earlier point in time, where the condition was recognized or predicted by system 200 based on data associated with a later point in time. Data that includes factors from different time periods, including later time periods where a condition was discovered or diagnosed, can be used to train system 200 (along with human-interaction and/or regression data, for example, and/or updated data sources such as data sources 230) through machine-learning processes, so that more patients can be diagnosed with a condition earlier in time.

In an illustrative embodiment, an interface such as interface 600, discussed below, indicates to a user that a prediction for an unknown value, such as a medical condition or an input material (in addition to its likelihood) is trending or shifting, for example in a recent time frame and/or in a relevant geographical area (by location of a patient, for example, or according to one or more geographic data points within an EMR or other data source). A user 204 can view individual factors 222, or locations or dates, associated with a trend or shift, for example by selecting a patient or list of cohorts 250 using interface 600. User 204 can also view additional predictions for an unknown value, including in some cases by making a selection and with predictions ranked by likelihood, or with a display of which predictions have shared symptoms and/or unique symptoms. In one case, output 186 includes a user interface 600 that can aid a user 204 by creating a diagnosis plan based on one or more predictions and/or underlying factors that may provide a roadmap or points of distinction as actions to be followed (for example by collecting data identified as the most useful based on a specific unknown value or gap in a record) in order to confirm a diagnosis, for example.

Figure 6:
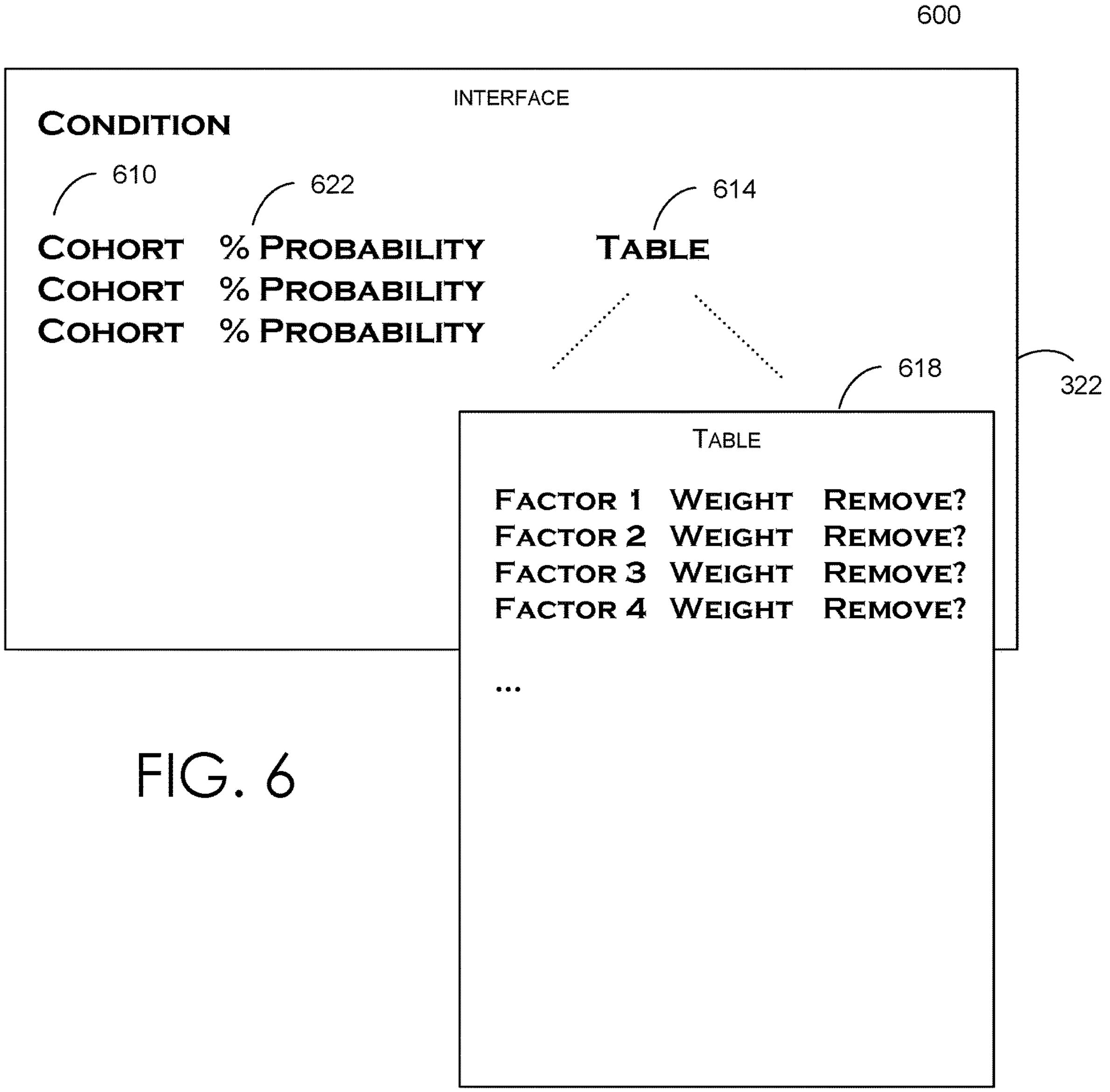
FIG. 6 is an exemplary user interface provided in accordance with one or more embodiments of the present invention.

As shown in FIG. 6, Table 1 can be displayed to user 204, for example via interface 600, and user 204 has the option to remove one or more factors (e.g., Factors 1-4), in some cases by making a selection such as by touching a "Remove?" button or by dragging one or more factors to an edge of interface 600. User 204, in some cases, can select each factor or all factors in order to view additional information regarding reach factor, such as inclusion criteria (for example, for a factor of elevated temperature, a medical professional may want to view or adjust this factor to a certain degree, for example an elevated temperate in a particular range that is potentially more associated with infection than other fevers). In some cases one ore patients are removed from consideration during analyses or within results b user 204, and such information can be used by system 200 as input to perform future analyses and to refine the accuracy or usefulness of the results. The selections by user 204 regarding one or more factors or patients can lead to additional menus or tables, while a master screen may continue to be displayed or may be hidden from view, and either Table 1 or a master screen such a dashboard can provide options via interface 600 for user 204 to remove certain characteristics or patients, and to provide this feedback to system 200.

In some cases, user 204 uses Table 1 or another aspect of an interface 600 to affect the weight assigned to one or more factors or patients. For example, user 204 may know that one factor is a frequent false positive for some reason (a concurrent outbreak of another condition, or a local anomaly, etc.) and user 204 can select to reduce the weight of a factor, such as certain flu symptoms, that overlap with a current epidemic or pocket of flu illnesses, instead of removing the factor. Alternatively user 204 can add weight to one or more factors, for example if an age group or prior surgery is believed to be strongly correlated with a condition based on a suggestion from system 200 (as determined by system 200 based on analyses of data) or based on user actions detected by system 200 in some cases. In embodiments, user 204 selects a recommendation from system 200 to increase the weight of a factor for a prior surgery to double the weight given to one or more other factors, while user 204 can also reduce the weight given to age or other demographics for the same analysis at the same time, for example if system 200 suggests the data may be skewed or biased with respect to such a factor. User 204 can observe the differences in weighting or removing various factors such as Factors 1-4 in FIG. 6 (Table 1) including in real-time or near real-time, because system 200 can recalculate or update results based on adjustments to underlying factors or patients considered. This permits several hypotheses to be explored.

A medical professional can evaluate a patient with limited to no medical history or diagnoses available, and/or with limited to no communication abilities, for example using embodiments of the present invention. Known information about the patient from a physical examination (such as temperature, blood pressure, age, etc.) or as conveyed to the extent possible, can be used by system 200 to generate an output of potential conditions impacting or likely to impact the patient including a treatment plan for the patient (which may include one or more prescriptions).

User 204 such as a curator of system 200 or data sources 230, or an end user, for example, can select and view a history of likelihoods or probabilities for one or more conditions for one or more patients or patient groups, including the users who entered predicted or actual diagnoses; and which information was adjusted (e.g., the content of data such as age increasing or the patient's temperature as measured, or the inclusion or weight of one or more factors) over time. Embodiments of system 200 can provide continuous access to data that is updated based on additional patient records, user interaction component 254 data, one or more regression analyses, and/or new or updated data sources 230, with layers or tags used to access or learn of updates to the data.

Embodiments can display unavailable factors where no information is present, or embodiments can display changes in the availability of factors for one or more patients. In some cases, two or more factors are analyzed in combination, for detection of a joint or compounding correlation, or for determination of a candidate condition's identity or probability based on a correlation between the balance of the factors associated with a known condition and the balance of the factors present or analyzed for a candidate condition. System 200 can consider how many unknown values, for example blank diagnoses or missing inputs, exist for each candidate that system 200 or a user determines should be included, and system 200 can consider or weight these various gaps as part of determining initial criteria or the certainty of predictions.

System 200 can respond to recent increases in certain factors in the population or patient group, or to recent increases in correlations of one or more factors to one or more conditions. Recent increases can be defined by amount and time period by a curator or an entity that includes end users, for example. System 200 can also respond, for example by pushing updated actions such as predictions, recommended factors, or treatment plans, to increases in correlations between factors and conditions in specific patient groups (e.g., post-surgery, men over a certain age, transplant recipients, etc.).

In embodiments, user 204 is an end user researcher or other professional who uses system 200 to present or distribute epidemiological data, including in some cases parallel or comparison information that reflects the influence of using factors as described herein to determine additional patients to include in association with a condition. This information can be presented for selection so that it can be compared, including over time, and updated. In some cases, system 200 is used to analyze historical or stored information to identify patients that likely should have or could have received a diagnosis at a certain time point (and the factors that were present at the time for these patients), and this information can be used by system 200 along with information from later in time to check or train the accuracy of system 200 using real data where patients were later diagnosed or not with a condition.

Figure 3:
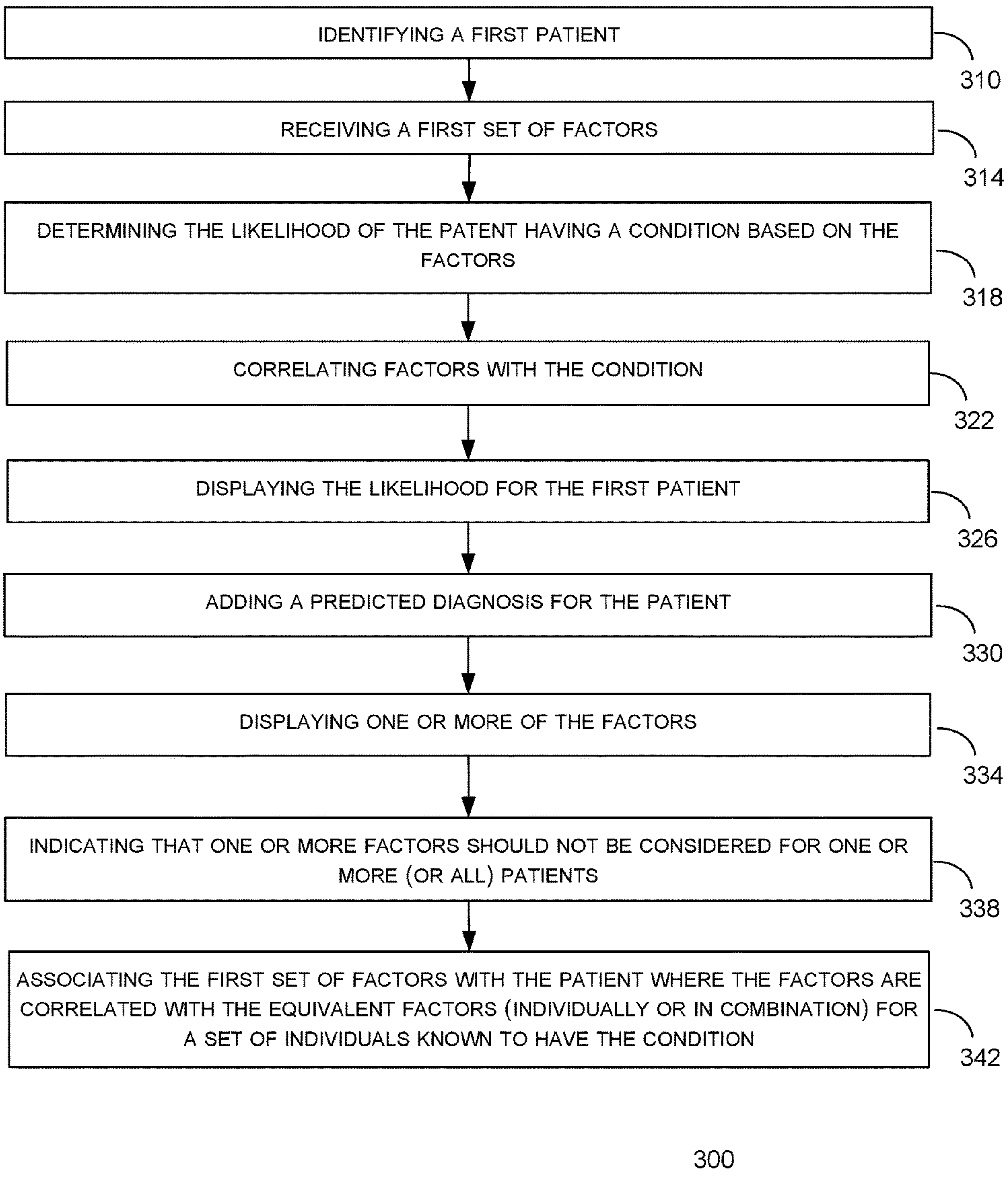
FIG. 3 is a flow chart illustrating one or more steps or actions performed by implementations involving systems according to an embodiment of the present invention.

FIG. 3 is a flow chart 300 illustrating one or more steps or actions performed by implementations involving systems according to an embodiment of the present invention. FIG. 3 includes identifying a first patient at 310, receiving a first set of factors at 314, and determining the likelihood of the patent having a condition based on the factors at 318, where the factors are correlated with the condition at 322, and FIG. 3 further includes displaying the likelihood for the first patient at 326. These steps are an example only, and some embodiments further include adding a predicted diagnosis for the patient at 330, and displaying one or more of the factors at 334. In some cases, a user such as user 204 or information from a user interaction component 254 indicates that one or more factors should not be considered for one or more (or all) patients at 338. In some cases, the first set of factors are associated with the patient and are correlated with the same factors (individually or in combination) for a set of individuals known to have the condition, as shown at 342, and a user 204 or a system 110 indicates that one or more of the individuals known to have the condition should not be considered by system 110, for example as part of a regression analysis. In embodiments, system 110 suggests additional factors such as factors 222 that correlate with the condition or with factors associated with individuals known to have the condition.

In embodiments, system 200 can identify and flag unexpected interactions or side effects for one or more treatments such a medication or therapy, including interactions with other lifestyle habits or choices, or as correlated in certain geographic areas or by time frame, such as when temperatures in an area have reached a certain degree or wet-bulb globe temperature for a minimum number of consecutive days within a two-month period, for example. In some cases system 200 uses one or more correlations between factors such as factors 222, and/or correlations between one or more factors 222 and potential medications or treatments, for example by treating a medication (or treatment option or update) for a patient as a condition and determining correlations with one or more factors that indicate a negative interaction with one or more medications (or treatment options or updates), in some cases when combined with one or more other factors, which can include other medications or treatment options or updates, or habits or behavioral choices, demographic information, and/or factors associated with negative side effects, for example.

Figure 4:
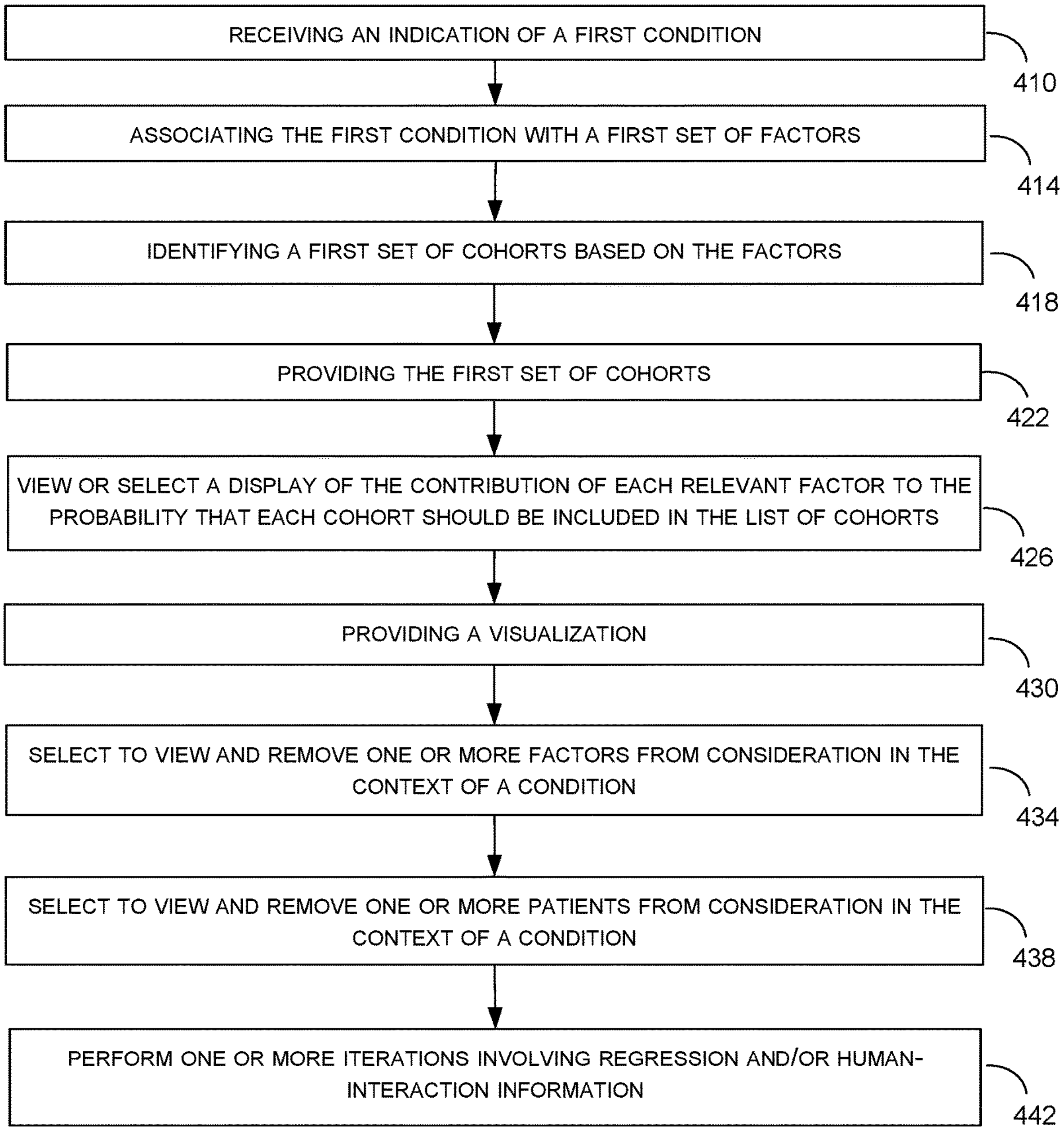
FIG. 4 is a flow chart illustrating one or more steps or actions performed by implementations involving systems according to an embodiment of the present invention.

FIG. 4 is a flow chart illustrating one or more steps or actions performed by implementations involving systems according to an embodiment of the present invention, for example for creating (and in some cases refining or updating) a list of cohorts 250 that can be displayed to user 204. FIG. 4 includes receiving an indication of a first condition at 410, associating the first condition with a first set of factors at 414, and identifying a first set of cohorts based on the factors at 418. In embodiments, a step of providing the first set of cohorts is included at 422, which can be listed or displayed by one or more devices such as computing device 114 or another device in communication with system 200, and user 204 can view or select a display of the contribution of each relevant factor to the probability that each cohort should be included in the list of cohorts, before or after iteration(s) as described herein, at 426 (in embodiments, a probability for each cohort including potential cohorts on a list of cohorts 250 can change, for example an increase from a first percentage such as 75% to a second percentage such as 81% after one or more iterations, and in some cases the probability over 80% obtained after iteration(s) that may be based on new data and/or adjustments, is over a threshold, such as 80%, which causes the cohort with a probability of 81% to be displayed to a user 204).

User 204 can be provided with a visualization at 430 of the overlap of various factors 222 with each other (such as factors relevant to the probabilities relating to each cohort), and/or the overlap of various factors 222 with one or more factors associated with a condition according to data sources 230 or system 200 (including contributions from human interaction component 254, as considered during regression analysis and/or iterations, in some cases).

In one example, user 204 can select to view and remove one or more factors from consideration in the context of a condition for example, where it is removed for an individual cohort including potential cohorts identified in a list of cohorts 250, or removed for all cohorts in system 200 with respect to one or more specific analyses or with respect to all analyses, as shown at 434. In embodiments, user 204 can select to view and remove one or more patients from consideration in the context of a condition at 438, whether the patient has a known diagnosis of a condition or where the patient does not have a known diagnosis of the condition (and may therefore appear on a list of cohorts 250, in some cases). In some cases, one or more iterations involving regression and/or human-interaction information result in a new set of cohorts 250 as shown at 442, which can overlap with an earlier set or show no change, or may show a change in the cohorts listed, the likelihoods for their inclusion, and/or changes due to a change in a threshold likelihood used to create a list of cohorts 250.

Figure 5:
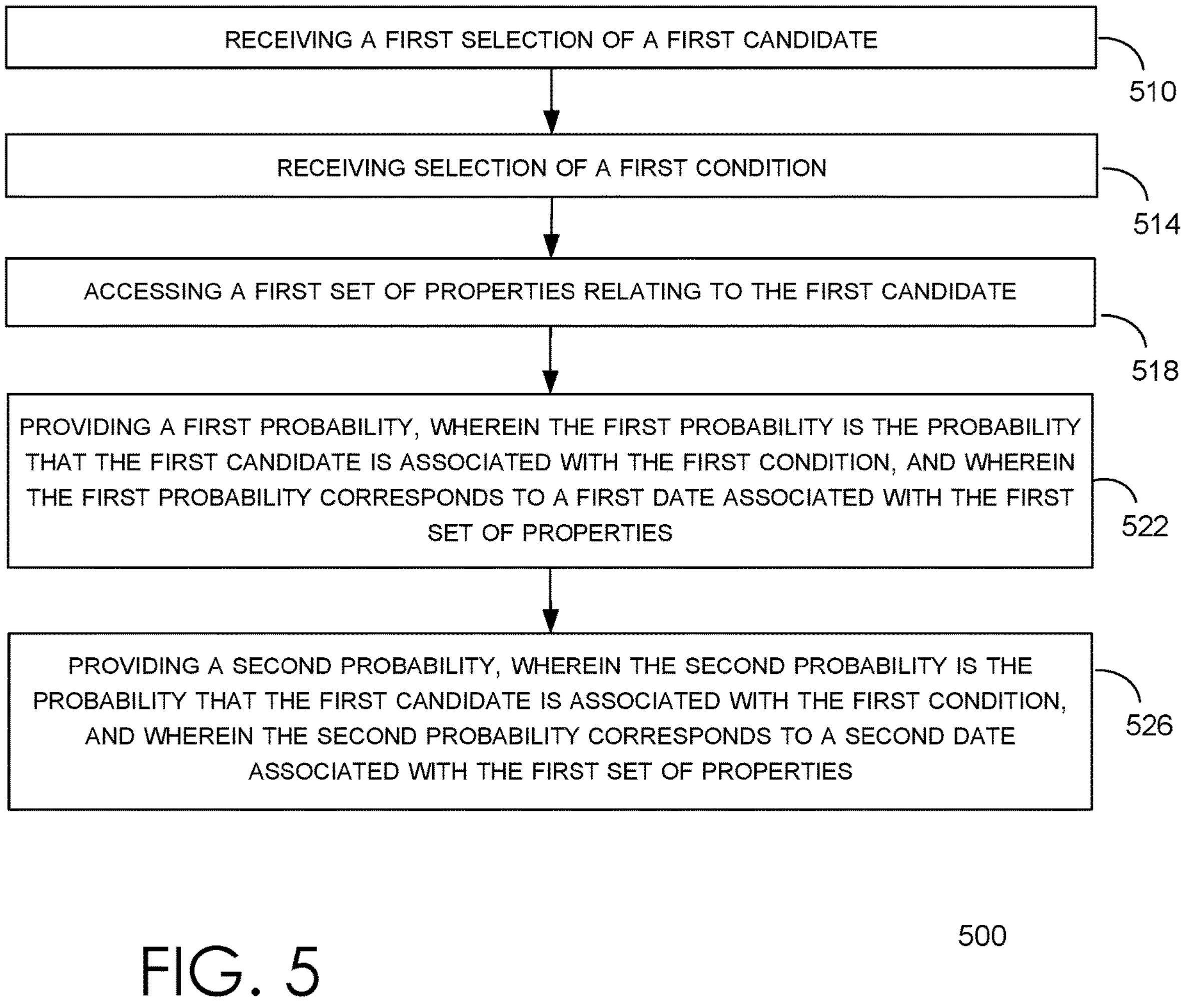
FIG. 5 is a flow chart illustrating one or more steps or actions performed by implementations involving systems according to an embodiment of the present invention.

FIG. 5 is a flow chart 500 illustrating one or more steps or actions performed by implementations involving systems according to an embodiment of the present invention. FIG. 5 includes receiving a first selection of a first candidate at 510, receiving selection of a first condition at 514, and accessing a first set of properties relating to the first candidate at 518. FIG. 5 also includes providing a first probability, wherein the first probability is the probability that the first candidate is associated with the first condition, and wherein the first probability corresponds to a first date associated with the first set of properties, at 522.

Embodiments include providing a second probability, wherein the second probability is the probability that the first candidate is associated with the first condition, and wherein the second probability corresponds to a second date associated with the first set of properties (and in some cases is associated with a time frame surrounding a certain event that is considered a factor correlated to a condition or indicating a higher probability of a condition occurring), at 526. In some cases, a trend between the first and second probabilities is determined at 530, which can be used to flag or include a candidate in a cohort 250 relating to the first condition. User 204 can use an interface such as interface 600 to navigate underlying factor data, rules, and/or options for providing user interaction to system 200, and user 204 can view or analyze the factor(s) that contributed to each cohort's inclusion on list of cohorts 250 or to a change in probability.

FIG. 6 is an exemplary user interface 600 provided in accordance with one or more embodiments of the present invention. A user such as user 204 can access interface 600 using a device such as computing device 114, remote from other devices and components of system 110, in embodiments. Interface 600 allows user 204 to select a condition, such as OUD, and to view or select the current members of this cohort (shown as 83 members in FIG. 2), in embodiments, and/or user 204 can select options using interface 600 to request that system 110 create a cohort.

User 204 can view trends of risk for each condition for potential member of a cohort, for example if a patient has a change or event such as a loss of employment, system 110 can communicate to a user 204 that the patient has recently experienced (in the last two weeks, for example) a spike in risk or an increase above a threshold within the time frame identified by a user or a system 110. In embodiments, this causes outreach or other treatment for the patient such as an appointment or medication, or a social wellness visit, or testing for a condition to be ordered. Interface 600 can include estimated predictions 610 displayed alongside an option 614 to view a table 618 of factors (e.g., factors 222) considered or used to determine predictions 610, where the table can be a list, such as list of selectable factors with accessible explanations, or the table can include one or more pieces of information regarding one or more factors for viewing by a user.

User 204 such as a medical professional can use interface 600 near the time of diagnosis or at any time pre-, during, or post-treatment, for example, to cause entries or updates to patients' EMRs or other records. User 204 can use exemplary interface 600 of an embodiment of system 200 to see predictions 610 and likelihoods 622 for one or more patients, such as patients with likelihoods 622 above a threshold or in the top amount of results, for example to output a plan relating to resources of a medical treatment or other facility. In some cases, an interface 600 associated with system 200 allows user 204 to select a cohort based on patients or a condition, and with one click or selection, user 204 is able to view all known patients in a cohort (as diagnosed or as confirmed or audited by embodiments) and all unknown patients likely to be members of a cohort, such as those in list of cohorts 250 in FIG. 2, which can trigger treatments including interviews or patient visits with patients likely to be members of a cohort.

As one example, a hospital director or a risk-analyzing entity is a user 204 and accesses an interface 600 in order to cause a display of patients currently in a medical facility including patients that are (1) diagnosed for a condition such as an antibiotic-resistant infection or were recorded as having that condition according to a code or standard description, or were diagnosed and system 200 confirmed or did not remove them from a set of patients known to have the condition; and/or (2) have an over 75% likelihood of having an antibiotic-resistant infection based on data from the last two months, for example, or based on a certain upward trend of likelihood of having the condition, in some cases with an initial cohort 250 or certain factors 222 relating to a narrowed geographic range (for example, patients with exposure to one or more facilities or travel to certain locations, or prior exposure to certain antibiotics).

An interface such as interface 600 can scale and adjust for use by remote or mobile medical devices or for larger presentation screens, as examples. User interface 600 can include a graphical display of a set of initial cohorts 250 that can be selected, in order to view a graphical display of the factors 222 contributing to the likelihood of each cohort developing or having a condition. In embodiments, a user 204 of user interface 600 can adjust the weights assigned to certain factors, or adjust the weight assigned to certain user interactions association with user interaction component 254, with a graphical display updating to match and showing the patients removed or added by the adjustment, or the shift in probabilities for each patient.

The exemplary modules in diagram 100 and discussed herein are suitable for use in implementing embodiments of the present invention. The modules are merely an example of one suitable computing system environment and are not intended to suggest any limitation as to the scope of use or functionality of embodiments of the present invention. Neither should the computing system environment be interpreted as having any dependency or requirement related to any single module/component or combination of modules/components illustrated therein. Embodiments of the present invention might be operational with numerous other computing system environments or configurations. Examples of computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. A system having one or more hardware processors configured to facilitate a plurality of operations, the operations comprising:

accepting a first selection of an individual;

accepting a second selection of a condition;

accessing a first set of information that relates to the individual and corresponds to a first date;

configuring a set of learning models, wherein configuring the set of learning models (a) comprises training a number-m of multiple machine-learning electronic models of differing model types based on data that includes factors from three or more differing time periods in which a condition was discovered or diagnosed, and based on content selected from factor data relating to the factors, condition data relating to the condition and indicated by the factor data, and temporal data relating to the three or more differing time periods, and (b) configures the set of learning models to generate an estimate of a likelihood of the condition at a time earlier than a time at which the condition was historically recorded as discovered or diagnosed in the data;

utilizing the number-m of multiple machine-learning electronic models to perform two or more machine-learning processes via the one or more hardware processors and to select, from stored information, a corresponding number-n of multiple factors relating to the condition, wherein (a) the two or more machine-learning processes comprise differing algorithm types selected from a regression analysis algorithm, an association-rule algorithm, a clustering algorithm, an instance-based algorithm, a reinforcement-learning algorithm, and a deep-learning algorithm, (b) the number-n of multiple factors are selected based on a cross-validation among the two or more machine-learning processes, (c) the two or more machine-learning processes implement a quadratic regression machine-learning electronic model, and (d) outputs of the quadratic regression machine-learning electronic model are used as inputs to one or more further calculations to iterate the selection of the number-n of multiple factors;

identifying, based on the first set of information, an analysis via the one or more hardware processors of two or more of the corresponding number-n of multiple factors, and the condition:

a first estimate of a likelihood of the individual being associated with the condition at a first time frame corresponding to the first date;

accessing a second set of information that relates to the individual and corresponds to a second date;

identifying, based on the second set of information and the condition:

a second estimate of the likelihood of the individual being associated with the condition at a second time frame corresponding to the second date;

identifying a rate of change utilizing (a) the first estimate of the likelihood of the individual being associated with the condition, at the first time frame corresponding to the first date and (b) the second estimate of the likelihood of the individual being associated with the condition at the second time frame corresponding to the second date;

determining whether the rate of change meets a threshold rate of change; and in response to determining that the rate of change meets the threshold rate of change:

generating output information for presentation via an electronic interface, wherein the output information indicates f (a) a particular likelihood of the individual having the condition, the particular likelihood being based on the first estimate and the second estimate and (b) the rate of change.

2. The system of claim 1, wherein the condition includes an opioid-use disorder condition, and wherein the operations further comprise: prior to the individual receiving a recognized diagnosis of the opioid-use disorder condition, updating an electronic health record associated with the individual based on the first estimate.

3. The system of claim 1, wherein the operations further comprise: receiving an indication that a first factor from the corresponding number-n of multiple factors should be removed; and determining a second estimate based on a subset, of the corresponding number-n of multiple factors, that does not include the first factor.

4. The system of claim 1, wherein the operations further comprise providing a second set of factors as suggested factors to be added to the corresponding number-n of multiple factors.

5. The system of claim 1, wherein determining the first estimate is based on a first regression analysis.

6. The system of claim 5, wherein determining the first estimate is based further on information associated with one or more user-interface interactions.

7. The system of claim 5, wherein determining the first estimate is based further on a second regression analysis, and wherein the second regression analysis is based at least in part on the information associated with one or more user-interface interactions.

8. One or more non-transitory media having instructions that, when executed by one or more hardware processors, cause the one or more hardware processors to facilitate a plurality of operations for analyzing information over a time period, the operations comprising:

accepting a first selection of an individual;

accepting a second selection of a condition;

accessing a first set of information that relates to the individual and corresponds to a first date;

configuring a set of learning models, wherein configuring the set of learning models (a) comprises training a number-m of multiple machine-learning electronic models of differing model types based on data that includes factors from three or more differing time periods in which a condition was discovered or diagnosed, and based on content selected from factor data relating to the factors, condition data relating to the condition and indicated by the factor data, and temporal data relating to the three or more differing time periods, and (b) configures the set of learning models to generate an estimate of a likelihood of the condition at a time earlier than a time at which the condition was historically recorded as discovered or diagnosed in the data;

utilizing the number-m of multiple machine-learning electronic models to perform two or more machine-learning processes via the one or more hardware processors and to select, from stored information, a corresponding number-n of multiple factors relating to the condition, wherein (a) the two or more machine-learning processes comprise differing algorithm types selected from a regression analysis algorithm, an association-rule algorithm, a clustering algorithm, an instance-based algorithm, a reinforcement-learning algorithm, and a deep-learning algorithm, (b) the number-n of multiple factors are selected based on a cross-validation among the two or more machine-learning processes, (c) the two or more machine-learning processes implement a quadratic regression machine-learning electronic model, and (d) outputs of the quadratic regression machine-learning electronic model are used as inputs to one or more further calculations to iterate the selection of the number-n of multiple factors;

identifying, based on the first set of information, an analysis via the one or more hardware processors of two or more of the corresponding number-n of multiple factors, and the condition:

a first estimate of a likelihood of the individual being associated with the condition at a first time frame corresponding to the first date;

accessing a second set of information that relates to the individual and corresponds to a second date;

identifying, based on the second set of information and the condition:

a second estimate of the likelihood of the individual being associated with the condition at a second time frame corresponding to the second date;

identifying a rate of change utilizing (a) the first estimate of the likelihood of the individual being associated with the condition, at the first time frame corresponding to the first date and (b) the second estimate of the likelihood of the individual being associated with the condition at the second time frame corresponding to the second date;

determining whether the rate of change meets a threshold rate of change; and in response to determining that the rate of change meets the threshold rate of change:

generating output information for presentation via an electronic interface, wherein the output information indicates (a) a particular likelihood of the individual having the condition, the particular likelihood being based on the first estimate and the second estimate and (b) the rate of change.

9. The one or more non-transitory media of claim 8, wherein the operations further comprise identifying an upward trend in the likelihood of the individual being associated with the condition as a relatively steep upward trend and providing an output, via the electronic interface, identifying that the upward trend is a relatively steep upward trend.

10. The one or more non-transitory media of claim 8, wherein the rate of change indicates a change in likelihood per change in date, and wherein the second set of information includes one or more events not present in the first set of information.

11. The one or more non-transitory media of claim 8, wherein accessing the second set of information includes ignoring one or more aspects, of the second set of information, identified by a user-interface interaction.

12. The one or more non-transitory media of claim 8, wherein the operations further comprise: prior to the individual receiving any recognized diagnosis of the condition, updating an electronic health record associated with the individual based on information selected from a group comprising the first estimate, the second estimate, and the rate of change.

13. The one or more non-transitory media of claim 8, wherein:

determining the first estimate comprises identifying a first probability that the individual has the condition at the first date, determining the second estimate comprises identifying a second probability that the individual has the condition at the second date, and the operations further comprise comparing the first estimate and the second estimate to determine the rate of change.

14. The one or more non-transitory media of claim 8, wherein the three or more differing time periods comprise at least a baseline time period and a plurality of later time periods subsequent to the baseline time period, and wherein the operations further comprise identifying an upward trend, in the likelihood of the individual being associated with the condition, based at least on (a) the first estimate, (b) the second estimate, (c) the first date, and (d) the second date.

15. The one or more non-transitory media of claim 8, wherein the operations further comprise identifying a spike associated with an upward trend between the first estimate and the second estimate.

16. The one or more non-transitory media of claim 8, wherein the second estimate is determined based on a same analysis via the one or more hardware processors of a same number-n of multiple factors.

17. The one or more non-transitory media of claim 8, wherein the operations further comprise generating content of the output information that indicates an upward trend in the likelihood of the individual being associated with the condition; and displaying on a GUI corresponding to the electronic interface, each of (a) the particular likelihood of the individual having the condition, content identifying the particular likelihood based on the first estimate and the second estimate, (b) the rate of change, and (c) the upward trend.

18. The one or more non-transitory media of claim 8, wherein the operations further comprise re-training the number-m of multiple machine-learning electronic models using feedback-updating data comprising one or both of a system confirmation and an input based override.

19. The one or more non-transitory media of claim 8, wherein the training is performed using historical stored data and is updated based on feedback information comprising a subsequently-recorded diagnosis.

20. The one or more non-transitory media of claim 8, wherein the operations further comprise: drawing ambient environmental data from a connected smart-appliance associated with the individual; and re-training the number-m of multiple machine-learning electronic models based on particular factor data that includes the ambient environmental data.

21. A method for analyzing information over a time period, the method performed by one or more hardware processors and comprising:

accepting a first selection of an individual;

accepting a second selection of a condition;

accessing a first set of information that relates to the individual and corresponds to a first date;

configuring a set of learning models, wherein configuring the set of learning models (a) comprises training a number-m of multiple machine-learning electronic models of differing model types based on data that includes factors from three or more differing time periods in which a condition was discovered or diagnosed, and based on content selected from factor data relating to the factors, condition data relating to the condition and indicated by the factor data, and temporal data relating to the three or more differing time periods, and (b) configures the set of learning models to generate an estimate of a likelihood of the condition at a time earlier than a time at which the condition was historically recorded as discovered or diagnosed in the data;

utilizing the number-m of multiple machine-learning electronic models to perform two or more machine-learning processes via the one or more hardware processors and to select, from stored information, a corresponding number-n of multiple factors relating to the condition, wherein (a) the two or more machine-learning processes comprise differing algorithm types selected from a regression analysis algorithm, an association-rule algorithm, a clustering algorithm, an instance-based algorithm, a reinforcement-learning algorithm, and a deep-learning algorithm, (b) the number-n of multiple factors are selected based on a cross-validation among the two or more machine-learning processes, (c) the two or more machine-learning processes implement a quadratic regression machine-learning electronic model, and (d) outputs of the quadratic regression machine-learning electronic model are used as inputs to one or more further calculations to iterate the selection of the number-n of multiple factors;

identifying, based on the first set of information, an analysis via the one or more hardware processors of two or more of the corresponding number-n of multiple factors, and the condition:

a first estimate of a likelihood of the individual being associated with the condition at a first time frame corresponding to the first date;

accessing a second set of information that relates to the individual and corresponds to a second date;

identifying, based on the second set of information and the condition:

a second estimate of the likelihood of the individual being associated with the condition at a second time frame corresponding to the second date;

identifying a rate of change utilizing (a) the first estimate of the likelihood of the individual being associated with the condition, at the first time frame corresponding to the first date and (b) the second estimate of the likelihood of the individual being associated with the condition at the second time frame corresponding to the second date;

determining whether the rate of change meets a threshold rate of change; and in response to determining that the rate of change meets the threshold rate of change:

generating output information for presentation via an electronic interface, wherein the output information indicates (a) a particular likelihood of the individual having the condition, the particular likelihood being based on the first estimate and the second estimate and (b) the rate of change.

22. The method of claim 21, wherein the method is performed at least partially via one or more processors, and further comprising: processing an indication that an aspect associated with one or both of the first estimate and the second estimate should be removed, and determining an updated rate of change based on the processing.

23. The method of claim 22, further comprising: determining whether the updated rate of change meets the threshold rate of change; and in response to determining that the updated rate of change meets the threshold rate of change, generating an output for presentation via the electronic interface indicating one or both of an updated first estimate and an updated second estimate and further indicating the updated rate of change.

24. The method of claim 21, wherein determining the first estimate is based on a first regression analysis, and wherein determining the first estimate is based further on information associated with one or more user-interface interactions.

* * * * *